US012129483B2

(12) United States Patent
Zeltner et al.

(10) Patent No.: US 12,129,483 B2
(45) Date of Patent: Oct. 29, 2024

(54) COMPOSITIONS AND METHODS FOR MAKING SENSORY NEURONS

(71) Applicant: University of Georgia Research Foundation, Inc., Athens, GA (US)

(72) Inventors: Nadja Zeltner, Athens, GA (US); Vicente Kenyi Saito-Diaz, Athens, GA (US)

(73) Assignee: UNIVERSITY OF GEORGIA RESEARCH FOUNDATION, INC., Athens, GA (US)

( * ) Notice: Subject to any disclaimer, the term of this patent is extended or adjusted under 35 U.S.C. 154(b) by 107 days.

(21) Appl. No.: 17/555,581

(22) Filed: Dec. 20, 2021

(65) Prior Publication Data

US 2022/0195386 A1    Jun. 23, 2022

Related U.S. Application Data

(60) Provisional application No. 63/127,958, filed on Dec. 18, 2020.

(51) Int. Cl.
*C12N 5/0793* (2010.01)
*A61K 35/30* (2015.01)

(52) U.S. Cl.
CPC ............ *C12N 5/0619* (2013.01); *A61K 35/30* (2013.01); *C12N 2501/999* (2013.01); *C12N 2506/02* (2013.01); *C12N 2506/45* (2013.01); *C12N 2533/50* (2013.01)

(58) Field of Classification Search
CPC .............................. C12N 5/0619; C12N 5/062
See application file for complete search history.

(56) References Cited

U.S. PATENT DOCUMENTS

| | | |
|---|---|---|
| 9,453,198 B2 | 9/2016 | Studer |
| 2008/0268019 A1 | 10/2008 | Badylak |
| 2009/0123433 A1 | 5/2009 | Shroff |
| 2011/0296542 A1 | 12/2011 | Wang |
| 2015/0159135 A1 | 6/2015 | Davis |
| 2019/0093074 A1 | 3/2019 | Studer |

FOREIGN PATENT DOCUMENTS

WO    2011149762    12/2011

OTHER PUBLICATIONS

Nolbrant et al. Generation of high-purity human ventral midbrain dopaminergic progenitors for in vitro maturation and cerebral transplantation. Nature Protocols 2017, 12;9:1962-1979. (Year: 2017).*
Alshawaf, et al., "Phenotypic and Functional Characterization of Peripheral Sensory Neurons derived from Human Embryonic Stem Cells", Scientific Reports, 8(1):603 (2018).
Bibel, et al., "Neurotrophins: key regulators of cell fate and cell shape in the vertebrate nervous system", Genes Dev., 14(23):2919-2937 (2000).
Boisvert, et al., "The Specification and Maturation of Nociceptive Neurons from Human Embryonic Stem Cells", Sci. Rep., 5:16821 (2015).
Calder, et al., "Retinoic Acid-Mediated Regulation of GLI3 Enables Efficient Motoneuron Derivation from Human ESCs in the Absence of Extrinsic SHH Activation", J. Neurosci., 35(33):11462-81 (2015).
Caterina, et al., "The capsaicin receptor: a heat-activated ion channel in the pain pathway", Nature, 389(6653):816-824 (1997).
Chambers, et al., "Combined small-molecule inhibition accelerates developmental timing and converts human pluripotent stem cells into nociceptors", Nat. Biotechnol., 30(7):715-720 (2012).
De Crozé, et al., "Reiterative AP2a activity controls sequential steps in the neural crest gene regulatory network", PNAS, 108(1):155-160 (2011).
Delmas, et al., "Molecular mechanisms of mechanotransduction in mammalian sensory neurons", Nature Reviews Neuroscience, 12(3):139-153 (2011).
Dionisi, et al., "Primary proprioceptive neurons from human induced pluripotent stem cells: a cell model for afferent ataxias", Sci. Rep., 10(7752):1-12 (2020).
Donnelly, et al., "Non-canonical Ret signaling augments p75-mediated cell death in developing sympathetic neurons", J. Cell Biol., 217:3237-3253 (2018).
Ernsberger, "Role of neurotrophin signalling in the differentiation of neurons from dorsal root ganglia and sympathetic ganglia", Cell Tissue Res., 336(3):349-384 (2009).
Fattahi, et al., "Deriving human ENS lineages for cell therapy and drug discovery in Hirschsprung disease", Nature, 531(7592):105-109 (2016).
Goldstein, et al., "Generation of neural crest cells and peripheral sensory neurons from human embryonic stem cells", Methods Mol. Biol., 584:283-300 (2010).
Huang, et al., "Neurotrophins: Roles in Neuronal Development and Function", Annu. Rev. Neurosci., 24:677-736 (2011).
Ji, et al., "Wnt Signaling in Neural Crest Ontogenesis and Oncogenesis", Cells, 8(10):1173 (2019).
Lallemend, et al., "Molecular interactions underlying the specification of sensory neurons", Trends Neurosci., 35(6):373-381 (2012).
Ma, et al., "Neurogenin1 and neurogenin2 control two distinct waves of neurogenesis in developing dorsal root ganglia", Genes Dev., 13(13):1717-1728 (1999).

(Continued)

*Primary Examiner* — Allison M Fox
*Assistant Examiner* — Jennifer S Spence
(74) *Attorney, Agent, or Firm* — PABST PATENT GROUP LLP

(57) ABSTRACT

The three main peripheral sensory neuron (SN) subtypes, nociceptors, mechanoreceptors, and proprioceptors localize to dorsal root ganglia (DRG) and convey sensations such as pain, temperature, pressure and limb movement/position. Disclosed herein is a chemically defined differentiation protocol that generates all three SN subtypes from the same starting population, as well as methods to enrich for each individual subtypes. The protocol yields high efficiency and purity cultures that are electrically active and respond to specific stimuli. Their molecular character and maturity stage are described and evidence for their use as an axotomy model is exemplified. Cell populations and compositions formed from the resulting cells, as well as methods of their use for disease treatment, drug screening, and modeling of human disorders affecting SNs are also provided.

20 Claims, 19 Drawing Sheets

(56) References Cited

OTHER PUBLICATIONS

Marmigére, et al., "Specification and connectivity of neuronal subtypes in the sensory lineage", Nat. Rev. Neurosci., 8(2):114-127 (2007).

Menendez, et al., "Wnt signaling and a Smad pathway blockade direct the differentiation of human pluripotent stem cells to multipotent neural crest cells", PNAS, 108(48):19240-19245 (2011).

Mica, et al., "Modeling neural crest induction, melanocyte specification, and disease-related pigmentation defects in hESCs and patient-specific iPSCs", Cell Rep., 3(4):1140-1152 (2013).

Namer, et al., "Pain relief in a neuropathy patient by lacosamide: Proof of principle of clinical translation from patient-specific iPS cell-derived nociceptors", EBioMedicine, 39:401-408 (2019).

Nehme, et al., "Combining NGN2 Programming with Developmental Patterning Generates Human Excitatory Neurons with NMDAR-Mediated Synaptic Transmission", Cell Rep., 23(8):2509-2523 (2018).

Norcliffe-Kaufmann, et al., "Familial dysautonomia: History, genotype, phenotype and translational research", Prog. Neurobiol., 152:131-148 (2017).

Pla, et al., "The neural border: Induction, specification and maturation of the territory that generates neural crest cells", Dev. Biol., 444(Suppl 1): S36-538 S46 (2018).

Pomp, et al., "Generation of peripheral sensory and sympathetic neurons and neural crest cells from human embryonic stem cells", Stem Cells, 23(7):923-930 (2005).

Poole, et al., "Tuning Piezo ion channels to detect molecular-scale movements relevant for fine touch", Nat. Commun., 5:3520 (2014).

Quallo, et al., "G protein βγ subunits inhibit TRPM3 ion channels in sensory neurons", ELife, 6:e26138 (2017).

Rostock, et al., "Human vs. Mouse Nociceptors—Similarities and Differences", Neuroscience, 387:13-27 (2018).

Schrenk-Siemens, et al., "PIEZO2 is required for mechanotransduction in human stem cell-derived touch receptors", Nat. Neurosci., 18(1):10-6 (2015).

Simões-costa, et al., "Establishing neural crest identity: a gene regulatory recipe", Development, 142(2):242-257 (2015).

Sloan, et al., "Human Astrocyte Maturation Captured in 3D Cerebral Cortical Spheroids Derived from Pluripotent Stem Cells", Neuron., 95(4): 779-790.e6 (2017).

Sun, et al., "A central role for Islet1 in sensory neuron development linking sensory and spinal gene regulatory programs", Nat. Neurosci., 11(11):1283-1293 (2008).

Tchieu, et al., "A Modular Platform for Differentiation of Human PSCs into All Major Ectodermal Lineages", Cell Stem Cell, 21(3):399-410.e7 (2017).

Théveneau, et al., "Ets-1 confers cranial features on neural crest delamination", PLoS One, 2(11):e1142 (2007).

Wilson, et al., "Human peptidergic nociceptive sensory neurons generated from human epidermal neural crest stem cells (hEPI-NCSC)", PlosOne, 13(6): e0199996 (2018).

Wong, et al., "CryoPause: A New Method to Immediately Initiate Experiments after Cryopreservation of Pluripotent Stem Cells", Stem Cell Reports, 9(1):355-365 (2017).

Young, et al., "Characterizing human stem cell-derived sensory neurons at the single-cell level reveals their ion channel expression and utility in pain research", Mol. Ther., 22(8):1530-1543 (2014).

Zeltner, et al., "Capturing the biology of disease severity in a PSC-based model of familial dysautonomia", Nat. Med., 22(12):1421-1427 (2016).

Zimmer, et al., "Human iPSC-derived trigeminal neurons lack constitutive TLR3-dependent immunity that protects cortical neurons from HSV-1 infection", PNAS, 115:E8775-E8782 (2018).

Zou, et al., "Eya1 and Six1 are essential for early steps of sensory neurogenesis in mammalian cranial placodes", Development, 131(22):5561-5572 (2004).

* cited by examiner

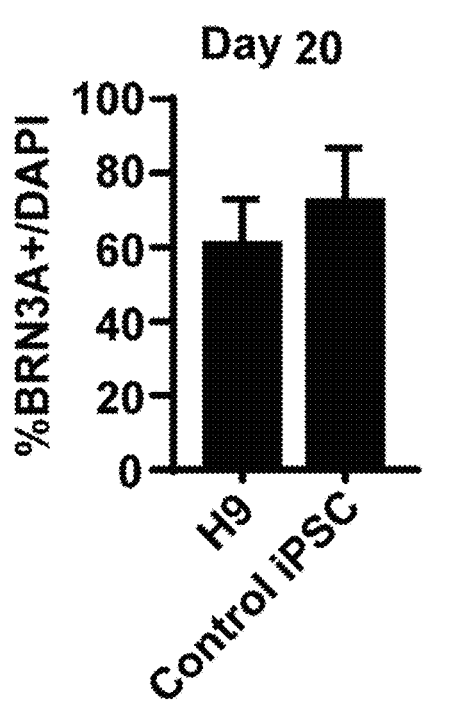
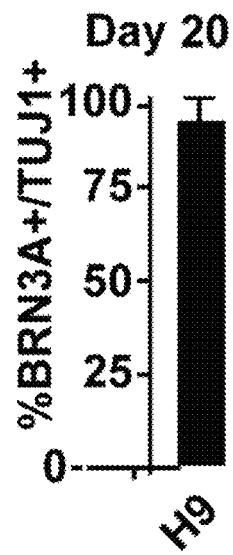
FIG. 1F
FIG. 1G
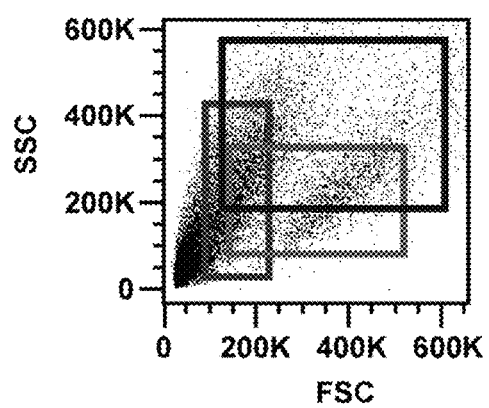
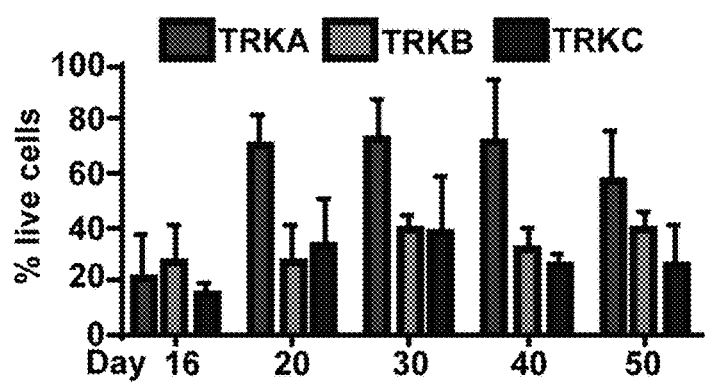
FIG. 1H
FIG. 1I

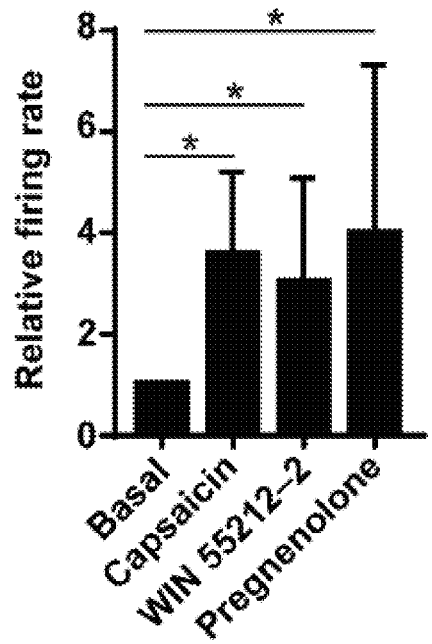
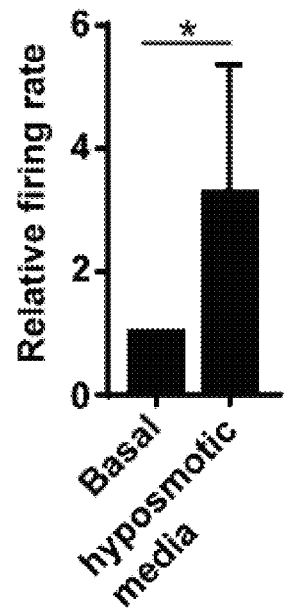
FIG. 2K  FIG. 2L
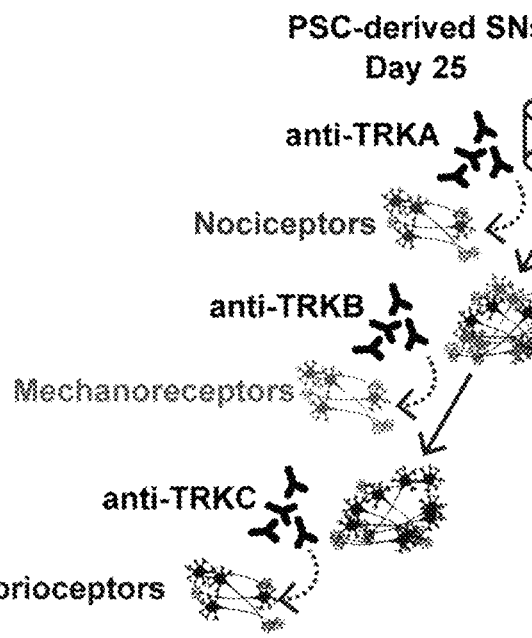
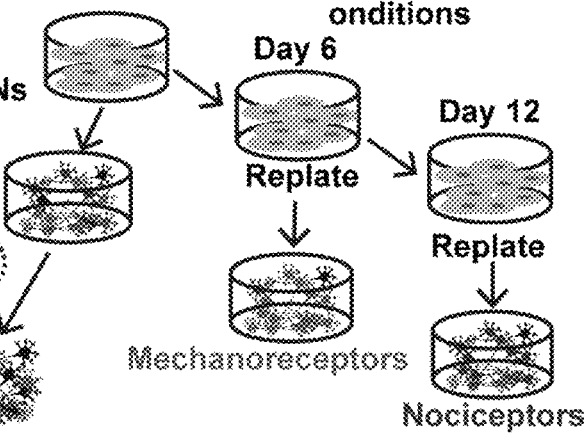
FIG. 3A

COMPOSITIONS AND METHODS FOR MAKING SENSORY NEURONS

CROSS-REFERENCE TO RELATED APPLICATIONS

This application claims benefit of and priority to U.S. Provisional Application No. 63/127,958, filed Dec. 18, 2020, which is hereby incorporated herein by reference in its entirety.

FIELD OF THE INVENTION

The field of the invention generally relates to compositions and methods of differentiating pluripotent cells into sensory neurons.

BACKGROUND OF THE INVENTION

Peripheral sensory neurons (SNs) localize to the dorsal root ganglia (DRG) that run parallel to the spinal cord. They innervate peripheral limbs, tissues, and organs. There are three main subtypes of SNs with specialized functions and innervation targets: 1) Nociceptors respond to noxious heat and chemical stimuli and convey pain sensations. They are typically small-to- medium-diameter, either thinly myelinated or unmyelinated, are specifically marked by the neurotrophin receptor TRKA (Lallemend & Ernfors, *Trends Neurosci.* 35, 373-381 (2012)). 2) Mechanoreceptors are large-diameter, myelinated neurons that express TRKB/TRKC and convey touch sensations. A subset has an extremely low threshold for activation (Poole, et al., *Nat Commun* 5, 3520 (2014)). 3) Proprioceptors are large-diameter TRKC+ neurons that sense limb movement and position (Lallemend & Ernfors, *Trends Neurosci.* 35, 373-381 (2012)).

DRG SNs originate from migrating neural crest cells (NCCs), which themselves originate from the neural plate border and are identified by markers such as SNAIL2, ETS1 and SOX10 (Pla & Monsoro-Burq, *Dev. Biol.* 444 Suppl 1, S36-538 S46 (2018)). SN specification originates from two main, distinct NCC migration waves, mostly defined in the mouse. First, mechanoreceptors and proprioceptors are specified by sensory-biased NCCs expressing NEUROGENIN2 (NGN2). RUNX3 expression is then upregulated promoting TRKC expression in proprioceptors or downregulated causing TRKB, TRKC and RET expression in mechanoreceptors. A second wave is characterized by the expression of NEUROGENIN1 (NGN1), and RUNX1 and gives rise to TRKA-expressing nociceptors (Marmigère & Ernfors, *Nat. Rev. Neurosci.* 8, 114-127 (2007)). Neurotrophins bind to specific TRK receptors to promote SN specification. Nerve growth factor (NGF), Brain-derived neurotrophic factor (BDNF) and Neurotrophin-3 (NT3) bind to TRKA, B and C, respectively (Huang & Reichardt, *Annu. Rev. Neurosci.* 24, 677-736 (2011)). Subtypes of mechanoreceptors and nociceptors express the neurotrophin receptor RET, which is activated by glial cell-line derived neurotrophic factor (GDNF) (Donnelly, et al., *J. Cell Biol.* 217, 3237-3253 (2018)). Despite these differences, all SN subtypes express the transcription factors BRN3A and ISLET1 (ISL1) (Lallemend & Ernfors, *Trends Neurosci.* 35, 373-381 (2012), Sun, et al., *Nat Neurosci* 11, 1283-1293 (2008)). To date, most of the studies of DRG neurons have been done in animal models. Thus, it is important to establish human models of this system to further knowledge of DRG and SNs in humans and study these cells' dysfunction in disease.

Pluripotent stem cell (PSC, including embryonic stem cells (ESCs) and induced pluripotent stem cells (iPSCs)) technology is a powerful tool to address this in SNs, to study SN diseases, to critically assess animal model-derived data, and to validate potential drug compounds.

There are several reports describing the differentiation of SNs from hPSCs (Alshawaf, et al., *Scientific Reports* 8, 603 (2018), Boisvert, et al., *Sci Rep* 5, 16821 (2015), Chambers, et al., *Nat. Biotechnol.* 30, 715-720 (2012), Goldstein, et al., *Methods Mol. Biol.* 584, 283-300 (2010), Namer, et al., *EBioMedicine* 39, 401-408 (2019), Pomp, et al., *Stem Cells* 23, 923-930 (2005), Schrenk-Siemens, et al., *Nat. Neurosci.* 18, 10-550 16 (2015), Young, et al., *Mol Ther* 22, 1530-1543 (2014), Wilson et al., PlosOne, June 28; 13(6): e0199996 (2018), Dionisi, et al., *Sci Rep* 10, 1-12 (2020)). Although they share some similarities, such as using some combination NGF, BDNF, and NT-3 growth factors, these protocols vary widely in their efficiency and the SN subtypes that they generate.

Thus, there remains a need for improved ways of preparing sensory neurons.

It is an object of the invention to provide compositions and methods for preparing sensory neurons.

SUMMARY OF THE INVENTION

Compositions and methods for making sensory neurons (SNs) are provided. The versatile compositions and methods can be used to derive SNs from pluripotent stem cell (PSC, including embryonic stem cells (ESCs) and induced pluripotent stem cells (iPSCs)). Preferred embodiments utilize feeder-free and/or chemically defined conditions.

The data presented below characterizes each developmental stage (from the neural plate border to SNs) and effectively quantify each SN subtype obtained using embodiments of the disclosed compositions and methods, and show that the methods can be used to make SN subtypes at the same proportions seen in the DRG in vivo. Furthermore, the culture conditions can be tuned or biased towards the generation of nociceptors or mechanoreceptors.

Additionally provided are compositions and methods for immunopanning as a gentle isolation techniques of specific SN subtypes.

In some embodiments, the methods include replating SN at a mature state. Experiments show the replated SN can regrow their axons and form functional synapses, indicating that they can be used as a model for axotomy.

In some embodiments, the composition and methods include one or more genetic modifications to the genome of the sensory neurons and/or introducing into the sensory neurons one or more nucleic acid expression constructs.

Thus, in some embodiments the compositions and methods are utilized for disease treatment (e.g., cell and/or gene therapy), for drug screen, and or to study various ailments of the peripheral nervous system (PNS).

BRIEF DESCRIPTION OF THE DRAWINGS

FIGS. 1A-1J show the generation and characterization of hESC-derived SNs. FIG. 1A is a timeline of NCC differentiation and conditions tested. FIG. 1B is a series of bar graphs showing flow cytometry quantification of CD49d+ NCCs. *$p<0.05$ using two-way ANOVA. FIG. 1C is a timeline of SN differentiation protocol (Top). Representative brightfield (BF) images for each indicated day 317 (bottom). FIG. 1D is a bar graph showing flow cytometry quantification of SN-biased NCCs stained for CD49d. *$p<0.01$,

**p<0.001, n.s., non-significant using one-way ANOVA. FIG. 1E is a diagram showing SN gene expression summary over differentiation. FIGS. 1F and 1G are bar graphs quantifying SN generation efficiency. Day 20 SNs were stained for TUJ1, BRN3A and DAPI (Top). Number of BRN3A+/all (DAPI+) cells and BRN3A+/neurons (TUJ1+) were quantified based on IF (below). FIGS. 1H and 1I are a scatter plot and bar graph respectively showing SN subtype quantification. The unstained cell population that corresponds to the expected subtype size was gated the SSC/FSC plot and then quantified based on its corresponding TRK receptor. Example: small cells were gated in left gate and of those ~70% stained+for TRKA at day 20. DAPI was used to exclude dead cells. FIG. 1J is a bar graph showing SNs express general (BRN3A, ISL1) and subtype-specific markers based on RT-qPCR. In all experiments N>4, bar graphs show mean±S.D.

FIGS. 2A-2L show characterization of late-stage SNs. FIG. 2B is a bar graph showing SNs express general mature markers by RT-qPCR. FIGS. 2B, 2C, and 2D are a series of bar graphs showing SNs express subtype-specific mature markers according to RT-qPCR. FIG. 2E is a plot showing a functional profile of SNs. NCCs were replated on MEA plates on day 12 and continued to differentiate. For each measurement day, 5 min were recorded and averaged over 6 wells. Statistical analysis was done comparing to day 20. FIGS. 2F-2J are a series of bar graphs showing quantification of average number of active electrodes (2F), number (2G) and duration of bursts (2H), and firing (2I) and burst frequency (2J) of SNs. FIGS. 2K and 2L are bar graphs showing SN activity is modulated by nociceptor (2K) and mechanoreceptor (2L) activation. SNs were incubated with nociceptor agonists or hypoosmotic media followed by 5 min recordings. Data is normalized to untreated control (basal). N>4 in FIGS. 2A-2D, N=3 in FIG. 2E-2L. Graphs show mean±S.D. *p<0.05, p<0.01, *p<0.001, ****p<0.0001 using one-way ANOVA.

FIGS. 3A-3F illustrate approaches for SN subtype enrichment. FIG. 3A is a schematic of exemplary proposed enrichment methods. FIG. 3B is a timeline of culture conditions to promote mechanoreceptor enrichment (top), and representative BF images of each day (below). FIG. 3C is a bar graph showing flow cytometry quantification of neurons expressing TRK receptors. The day when cells were replated and analyzed are indicated. FIGS. 3D and 3E are bar graphs, showing SNs differentiated from SN-biased NCC replated on day 6 express mechanoreceptor markers TRKB, RET, BRN3A, TUJ1, VGLUT3 and PRPH by 352 RT-qPCR. FIG. 3F is a bar graph showing SN activity is modulated by hypoosmotic media. SNs were incubated for 1 min prior to data acquisition. Data is normalized to untreated control (basal). In all experiments N>4. Graphs show mean±S.D. *p<0.05, using t-test with Welch's correction.

FIG. 4A is a timeline of differentiation highlighting quality control checkpoints to ensure a successful differentiation. FIG. 4B is a bar graph illustrating Checkpoint 2, by SOX10 expression (RT-qPCR) on day 8. FIGS. 4C and 4D are bar graphs illustrating Checkpoint 3, by BRN3A expression (IF image quantification on day 20 (4C and RT-qPCR (4D)). In all experiments N=3. Graphs show mean±S.D. *p<0.05, 362 p<0.01, *p<0.001, ****p<0,0001 using one-way ANOVA.

FIGS. 5A-5C are a series of bar graphs showing expression of the pluripotent marker OCT4 (5A) and NCC markers SOX10 (5B) and P75 (5C) in NCCs differentiated using each protocol tested. FIG. 5D is a schematic of markers expressed on each differentiation step (from pluripotent to NCC). FIGS. 5E and 5F are bar graphs showing gene expression by RT-qPCR of (5E) the pluripotency marker OCT4, neural plate border markers GATA2/3 and AP2a and (5F) premigratory neural crest markers PAX3, ETS1 and SNAIL2 in cells generated using the SN differentiation protocol in each indicated day. FIG. 5G is a bar graph showing expression off NCC markers SOX10, FOXS1 and SN marker BRN3A by RT-qPCR on each indicated day. FIG. 5H is a bar graph showing gene expression of potential contaminant progenitor cells generated during differentiation. FIG. 5I illustrates gene expression of potential contaminant neurons or differentiated cells generated during differentiation by RT-qPCR. FIG. 5J is a bar graph showing gene expression of myofibroblast and Schwann cell markers. In all experiments N>4. Graphs show mean±S.D. *p<0.05, **p<0.01, n.s. non-significant using two-way ANOVA.

FIG. 6A is a bar graph showing BRN3A expression timing. NCCs were replated on day 12 and RNA was isolated on the indicated days. BRN3A expression was measured by RT-qPCR. FIGS. 6B and 6C are line graphs showing a functional profile (#spikes (6B), Firing rate (Hz) (6C)) of late replate SNs. SNs were replated on day 30 on MEA plates. 5 min measurements were taken and the average number of spikes (left) and the firing rate (right) detected on each day and is shown. In all experiments N>3 Graphs show mean 49±S.D. *p<0.05 using one-way ANOVA.

FIG. 7A is a schematic of an initial approach. On day 12 of differentiation, NCCs were replated using SN differentiation media containing GDNF and the indicated growth factors and analyzed by flow cytometry. FIG. 7B is a bar graph showing quantification of SNs differentiated using enrichment media as indicated on 7A. SNs were stained with TRKA, TRKB and TRKC antibodies and quantified by flow cytometry. DAPI was used as viability dye. FIGS. 7C-7F are a series of scatter plots showing identification (7C) of subpopulation of noci- (7D), mechano- (7E), and proprioceptor (7F) enrichment by flow cytometry. Side scatter and forward scatter showing gated areas where each subtype is enriched and the percentages of each subpopulation are shown. FIG. 7G is a bar graph showing NGN2 and NGN1 waves are present during SN differentiation. RNA from SN-biased NCCs was obtained on each indicated day and NGN1 and NGN2 expression was measured by RT-qPCR. In all experiments N>4. Graphs show mean±S.D.

DETAILED DESCRIPTION OF THE INVENTION

I. Definitions

Figure 1A:
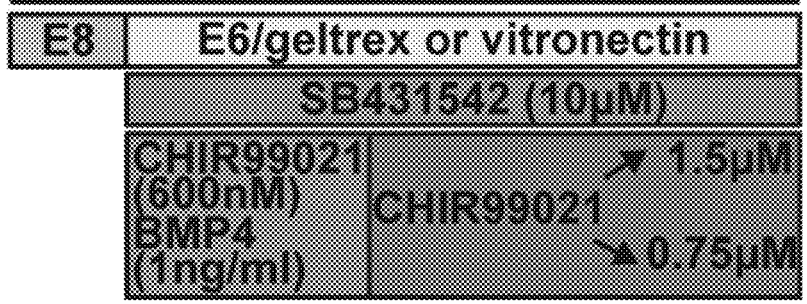

Recitation of ranges of values herein are merely intended to serve as a shorthand method of referring individually to each separate value falling within the range, unless otherwise indicated herein, and each separate value is incorporated into the specification as if it were individually recited herein.

All methods described herein can be performed in any suitable order unless otherwise indicated or otherwise clearly contradicted by context. The use of any and all examples, or exemplary language (e.g., "such as") provided herein, is intended merely to better illuminate the embodiments and does not pose a limitation on the scope of the embodiments unless otherwise claimed. No language in the specification should be construed as indicating any non-claimed element as essential to the practice of the invention.

As used herein, the term "about" or "approximately" means within an acceptable error range for the particular value as determined by one of ordinary skill in the art, which will depend in part on how the value is measured or determined, i.e., the limitations of the measurement system. For example, "about" can mean within 3 or more than 3 standard deviations, per the practice in the art. Alternatively, "about" can mean a range of up to 20%, e.g., up to 10%, up to 5%, or up to 1% of a given value. Alternatively, particularly with respect to biological systems or processes, the term can mean within an order of magnitude, e.g., within 5-fold, or within 2-fold, of a value.

As used herein, the term "a population of cells" or "a cell population" refers to a group of at least two cells. In non-limiting examples, a cell population can include at least about 10, at least about 100, at least about 200, at least about 300, at least about 400, at least about 500, at least about 600, at least about 700, at least about 800, at least about 900, at least about 1000 cells. The population may be a pure population comprising one cell type, such as a population of proprioceptors, or a population of undifferentiated stem cells. Alternatively, the population may comprise more than one cell type, for example a mixed cell population.

As used herein, the term "stem cell" refers to a cell with the ability to divide for indefinite periods in culture and to give rise to specialized cells. A stem cell refers to a stem cell that is from a human.

As used herein, the term "embryonic stem cell" refers to a primitive (undifferentiated) cell that is derived from pre-implantation-stage embryo, capable of dividing without differentiating for a prolonged period in culture, and are known to develop into cells and tissues of the three primary germ layers. A human embryonic stem cell refers to an embryonic stem cell that is from a human. As used herein, the term "human embryonic stem cell" or "hESC" refers to a type of pluripotent stem cells derived from early stage human embryos, up to and including the blastocyst stage, that is capable of dividing without differentiating for a prolonged period in culture, and are known to develop into cells and tissues of the three primary germ layers.

As used herein, the term "embryonic stem cell line" refers to a population of embryonic stem cells which have been cultured under in vitro conditions that allow proliferation without differentiation for up to days, months to years.

As used herein, the term "totipotent" refers to an ability to give rise to all the cell types of the body plus all of the cell types that make up the extraembryonic tissues such as the placenta.

As used herein, the term "multipotent" refers to an ability to develop into more than one cell type of the body.

As used herein, the term "pluripotent" refers to an ability to develop into the three developmental germ layers of the organism including endoderm, mesoderm, and ectoderm.

As used herein, the term "induced pluripotent stem cell" or "iPSC" refers to a type of pluripotent stem cell, similar to an embryonic stem cell, formed by the introduction of certain embryonic genes (such as OCT4, SOX2, and KLF4 transgenes) (see, for example, Takahashi and Yamanaka *Cell* 126, 663-676 (2006), herein incorporated by reference) into a somatic cell, for examples, CI 4, C72, and the like. An induced pluripotent stem cell may be prepared from any fully (e.g., mature or adult) or partially differentiated cell using methods known in the art. For example, but not by way of limitation, an induced pluripotent stem cell may be prepared from a fibroblast, such as a human fibroblast; an epithelial cell, such as a human epithelial cell; a blood cell such as a lymphocyte or hematopoietic cell or cell precursor or myeloid cell, such as a human lymphocyte, hematopoietic cell or cell precursor or human myeloid cell; or a renal epithelial cell, such as a human renal epithelial cell. In certain non-limiting embodiments, an induced pluripotent stem cell contains one or more introduced reprogramming factor associated with producing pluripotency. In certain non-limiting embodiments a human induced pluripotent stem cell is not identical to a human embryonic pluripotent stem cell.

As used herein, the term "somatic cell" refers to any cell in the body other than gametes (egg or sperm); sometimes referred to as "adult" cells.

As used herein, the term "somatic (adult) stem cell" refers to a relatively rare undifferentiated cell found in many organs and differentiated tissues with a limited capacity for both self-renewal (in the laboratory) and differentiation. Such cells vary in their differentiation capacity, but it is usually limited to cell types in the organ of origin.

As used herein, the term "neuron" refers to a nerve cell, the principal functional units of the nervous system. A neuron consists of a cell body and its processes—an axon and one or more dendrites. Neurons transmit information to other neurons or cells by releasing neurotransmitters at synapses.

As used herein, the term "proliferation" refers to an increase in cell number.

As used herein, the term "undifferentiated" refers to a cell that has not yet developed into a specialized cell type.

As used herein, the term "differentiation" refers to a process whereby an unspecialized embryonic cell acquires the features of a specialized cell such as a heart, liver, or muscle cell. Differentiation is controlled by the interaction of a cell's genes with the physical and chemical conditions outside the cell, usually through signaling pathways involving proteins embedded in the cell surface.

As used herein, the term "directed differentiation" refers to a manipulation of stem cell culture conditions to induce differentiation into a particular (for example, desired) cell type, such as sensory neurons or a subtype thereof such as nociceptors, mechanoreceptors and/or proprioceptors. As used herein, the term "directed differentiation" in reference to a stem cell typically refers to the use of small molecules, growth factor proteins, and other growth conditions to promote the transition of a stem cell from the pluripotent state into a more mature or specialized cell fate (e.g., sensory neurons or a subtype thereof such as nociceptors, mechanoreceptors and/or proprioceptors).

As used herein, the term "inducing differentiation" in reference to a cell refers to changing the default cell type (genotype and/or phenotype) to a non-default cell type (genotype and/or phenotype). Thus, "inducing differentiation in/of a stem cell" refers to inducing the stem cell (e.g., stem cell) to divide into progeny cells with characteristics that are different from the stem cell, such as genotype (e.g., change in gene expression as determined by genetic analysis such as a microarray) and/or phenotype (e.g., change in expression of a protein, such as one or more markers.

As used herein, the term "cell culture" refers to a growth of cells in vitro in an artificial medium for research or medical treatment.

As used herein, the term "culture medium" refers to a liquid that covers cells in a culture vessel, such as a Petri plate, a multi-well plate, and the like, and contains nutrients to nourish and support the cells. Culture medium may also include growth factors added to produce desired changes in the cells.

As used herein, the term "contacting" cells with a compound refers to placing the compound in a location that will allow it to touch the cell. The contacting may be accomplished using any suitable methods. For example, contacting can be accomplished by adding the compound to a tube of cells. Contacting may also be accomplished by adding the compound to a culture medium comprising the cells. Each of the compounds can be added to a culture medium comprising the cells as a solution (e.g., a concentrated solution). Alternatively or additionally, the compounds as well as the cells can be present in a formulated cell culture medium.

As used herein, the term "in vitro" refers to an artificial environment and to processes or reactions that occur within an artificial environment. In vitro environments exemplified, but are not limited to, test tubes and cell cultures.

As used herein, the term "in vivo" refers to the natural environment (e.g., an animal or a cell) and to processes or reactions that occur within a natural environment, such as embryonic development, cell differentiation, neural tube formation, etc.

As used herein, the term "expressing" in relation to a gene or protein refers to making an mRNA or protein which can be observed using assays such as microarray assays, antibody staining assays, and the like.

As used herein, the term "marker" or "cell marker" refers to gene or protein that identifies a particular cell or cell type. A marker for a cell may not be limited to one marker, markers may refer to a "pattern" of markers such that a designated group of markers may identity a cell or cell type from another cell or cell type.

As used herein, the term "derived from" or "established from" or "differentiated from" when made in reference to any cell disclosed herein refers to a cell that was obtained from (e.g., isolated, purified, etc.) a parent cell in a cell line, tissue (such as a dissociated embryo, or fluids using any manipulation, such as, without limitation, single cell isolation, cultured in vitro, treatment and/or mutagenesis using for example proteins, chemicals, radiation, infection with virus, transfection with DNA sequences, such as with a morphogen, etc., selection (such as by serial culture) of any cell that is contained in cultured parent cells. A derived cell can be selected from a mixed population by virtue of response to a growth factor, cytokine, selected progression of cytokine treatments, adhesiveness, lack of adhesiveness, sorting procedure, and the like.

An "individual" or "subject" herein is a vertebrate, such as a human or non-human animal, for example, a mammal. Mammals include, but are not limited to, humans, primates, farm animals, sport animals, rodents and pets. Non-limiting examples of non-human animal subjects include rodents such as mice, rats, hamsters, and guinea pigs; rabbits; dogs; cats; sheep; pigs; goats; cattle; horses; and non-human primates such as apes and monkeys.

As used herein, the term "disease" refers to any condition or disorder that damages or interferes with the normal function of a cell, tissue, or organ.

As used herein, the term "treating" or "treatment" refers to clinical intervention in an attempt to alter the disease course of the individual or cell being treated, and can be performed either for prophylaxis or during the course of clinical pathology. Therapeutic effects of treatment include, without limitation, preventing occurrence or recurrence of disease, alleviation of symptoms, diminishment of any direct or indirect pathological consequences of the disease, preventing metastases, decreasing the rate of disease progression, amelioration or palliation of the disease state, and remission or improved prognosis. By preventing progression of a disease or disorder, a treatment can prevent deterioration due to a disorder in an affected or diagnosed subject or a subject suspected of having the disorder, but also a treatment may prevent the onset of the disorder or a symptom of the disorder in a subject at risk for the disorder or suspected of having the disorder.

As used herein, the term "an effective amount" or "effective amounts" refers to an amount of a molecule that is sufficient to achieve a desired effect. In some examples, the amount is effective in directing the in vitro differentiating of stem cells into a population of differentiated cells expressing one or more desired markers. In certain embodiments, the population of differentiated cells includes cells expressing one or more desired marker.

As used herein, "transformed" and "transfected" encompass the introduction of a nucleic acid (e.g., a vector) into a cell by a number of techniques known in the art.

II. Methods of Making Differentiated Sensory Neurons

A versatile protocol for the generation of functional SNs that mimic the proportions of subtypes in the DRG has been developed. Several methods can be employed to isolate each of the specific SN subtypes, nociceptors, mechanoreceptors and proprioceptors from these cultures. This protocol can be adapted for a myriad of research interests ranging from studying the human DRG to investigating PNS diseases such as FD using patient-derived iPSCs that affect either all SN subtypes or each of the individual subtypes, and the work can be used to further advance numerous fields interested in studying the functions of, and diseases associated with, human SNs.

The protocol is exemplified in the experiments below, and may include any one or more compositions or methodologies described therein.

A. Starting Cells

Typically the methods include inducing differentiation of stems cells in vitro into sensory neurons, or one or more subtypes thereof such as nociceptors, mechanoreceptors, and/or proprioceptors. In certain embodiments, the stem cells are human stem cells. Non-limiting examples of human stem cells include human embryonic stem cells (hESC), human pluripotent stem cell (hPSC), human induced pluripotent stem cells (hiPSC), human parthenogenetic stem cells, primoridal germ cell-like pluripotent stem cells, epiblast stem cells, F-class pluripotent stem cells, somatic stem cells, cancer stem cells, or any other cell capable of lineage specific differentiation. In certain embodiments, the human stem cell is a human embryonic stem cell (hESC). In certain embodiments, the human stem cell is a human induced pluripotent stem cell (hiPSC). In certain embodiments, the stem cells are non-human stem cells. Non-limiting examples of non-human stem cells include non-human primate stem cells, rodent stem cells, dog stem cells, cat stem cells, horse stem cells, pig stem cells, etc. In certain embodiments, the stem cells are pluripotent stem cells. In certain embodiments, the stem cells are embryonic stem cells. In certain embodiments, the stem cells are induced pluripotent stem cells.

The cells can be autologous, e.g. derived from the subject, or syngeneic. Allogeneic cells can also be isolated from antigenically matched, genetically unrelated donors (identified through a national registry), or by using cells obtained or derived from a genetically related sibling or parent.

B. Culture Steps and Differentiation Factors

Prior to differentiation, plates are typically coated with a substrate such as Geltrex or vitronectin or Matrigel, and used to culture stem cells, followed by induction to differentiate into sensory neurons. Cells are fed and cultured over time and may include one, two, three, or more, but preferably only one replating. The cells can be cultured in a monolayer. Thus in some embodiments, the methods do not include forming neurospheres. In some embodiments, the methods are also free from a feeder layer.

It has been discovered that (i) initiating the differentiation the day of stem cell seeding (e.g., rather than 24 h later), (ii) lowering the concentration of Wnt signaling activator (e.g., CHIR99021) and, (iii) using vitronectin (VTN, rather than Geltrex) resulted in dense NC 'ridges'. Thus, in some embodiments, the disclosed methods include (i), (ii), (iii), or a combination thereof.

The disclosed methods and compositions can include one or more compositions or methods or steps thereof disclosed in U.S. Patent Application No. 2019/0093074 or U.S. Pat. No. 9,453,198, each if which is specifically incorporated by reference herein in its entirety.

The methods can include FGFR/VEGFR inhibition (e.g., SU-5402) and/or Notch inhibition (e.g., DAPT) and/or transforming growth factor beta (TGFβ)/Activin-Nodal signaling inhibition and/or wingless (Wnt) signaling activation. The methods can include BMP supplementation, e.g., BMP4. The methods thus can include culturing or otherwise contacting the cells with one or more FGFR/VEGFR and/or Notch and/or TGFβ/Activin-Nodal signaling inhibitors, and/or one or more Wnt signaling activators and/or one or more BMPs. Typically the inhibitor(s) and/or activator(s) and/or BMP(s) are used in a suitable combination and effective amounts and for sufficient duration to differentiate stems cells, and/or induce them to form and/or maintain them as sensory neurons, or a particular subpopulation thereof, e.g., as exemplified herein.

Non-limiting examples of inhibitors of FGFR family signaling are disclosed in WO2011/149762 which is incorporated by reference in its entirety, and are otherwise known in the art. In certain embodiments, the one or more inhibitor of FGF receptor family signaling is a small molecule selected from the group consisting of SU5402, PD-161570, PD-173074, derivatives thereof, and mixtures thereof. In certain embodiments, the one or more inhibitor of FGF receptor family signaling is SU5402. "SU5402" and "SU-5402" refers to a small molecule with a chemical formula of $C_{11}H_{16}N_2O_3$ and chemical name: 2-[(1,2-Dihydro-2-oxo-3H-indol-3-ylidene)methyl]-4-methyl-1H-pyrrole-3-propanoic acid. In some embodiments, the inhibitor of FGFR family signaling, e.g., SU5402, is used in a concentration ranging from 1 µM to 5 µM inclusive. A particularly preferred concentration is about 2.5 µM, or 2.5 µM.

In certain embodiments, the inhibitor of Notch signaling is a γ-secretase inhibitor. γ-secretase inhibitors are a class of agents that prevent the generation of the active domain of Notch molecules resulting in suppression of downstream Notch signaling. Non-limiting examples of γ-secretase inhibitors are DAPT, a tripeptide aldehyde inhibitor, a γ-secretase inhibitor XII, LY-411,575. In certain embodiments, the one or more inhibitor of Notch signaling is a small molecule selected from the group consisting of DAPT, a tripeptide aldehyde inhibitor, a γ-secretase inhibitor XII, LY-411,575, derivatives thereof, and mixtures thereof. In some embodiments, the inhibitor of Notch signaling, e.g., DAPT, is used in a concentration ranging from 1 µM to 5 µM inclusive. A particularly preferred concentration is about 2.5 µM, or 2.5 µM.

Non-limiting examples of inhibitors of TGFβ/Activin-Nodal signaling are disclosed in WO2011/149762, and are otherwise known in the art. In certain embodiments, the inhibitor of TGFβ/Activin-Nodal signaling is a small molecule selected from the group consisting of SB431542, derivatives thereof, and mixtures thereof. "SB431542" refers to a molecule with a number CAS 301836-41-9, a molecular formula of $C_{22}K_8N_4O_3$, and a name of 4-[4-(1,3-benzodioxol-5-yl)-5-(2-pyridinyl)-1H-imidazol-2-yl]-benzamide. In some embodiments, the inhibitor of TGFβ/Activin-Nodal signaling, e.g., SB431542, is used in a concentration ranging from 5 µM to 10 µM inclusive. A particularly preferred concentration is about 10 µM, or 10 µM.

Non-limiting examples of bone morphogenic proteins (BMPs) include BMP2, BMP4, BMP6, and BMP7. In some embodiments, the BMP, e.g., BMP4, is used in a concentration ranging from 0 ng/ml to 5 ng/ml inclusive. A particularly preferred concentration is about 1 ng/ml, or 1 ng/ml. BMP, e.g., BMP4 can be important, and is preferably used at the lower end of a range that gives the desired results, e.g., as discussed herein such as efficiently obtaining NC. Thus, in some embodiments the BMP, e.g., BMP4 is titrated, particularly down, to determine the best concentration, which may vary somewhat between different cell types, e.g., different hPSC lines.

In certain embodiments, the activator of Wnt signaling lowers GSK3β for activation of Wnt signaling. Thus, the activator of Wnt signaling can be a GSK3β inhibitor. Non-limiting examples of activators of Wnt signaling or GSK3β inhibitors are disclosed in WO2011/149762, and Calder et al., *J Neurosci*. 2015 Aug. 19; 35(33):11462-81, which are incorporated by reference in their entireties, and are otherwise known in the art. In certain embodiments, the activator of Wnt signaling is a small molecule selected from the group consisting of CHIR99021, derivatives thereof, and mixtures thereof "CHIR99021" (also known as "aminopyrimidine" or "3-[3-(2-Carboxyethyl)-4-methylpyrrol-2-methylidenyl]-2-indolinone") refers to IUPAC name 6-(2-(4-(2,4-dichlorophenyl)-5-(4-methyl-1H-imidazol-2-yl)pyrimidin-2-ylamino) ethylamino)nicotinonitrile. In some embodiments, the activator of Wnt signaling, e.g., CHIR99021, is used in a concentration ranging from 100 nM to 500 nM from days 0-2 and/or 0.25 µM to 1.5 µM from day 2 on, inclusive. In particular embodiments the activator of Wnt signaling, e.g., CHIR99021, is used at a concentration of 300 nM from day 0-2 and/or 0.75 µM chir from day 2 on.

In some embodiments, the concentration of Wnt signaling activator, e.g., CHIR99021, is used at a lower level than other methods of making sensory neurons. In particularly embodiments the concentration of Wnt signaling activator, e.g., CHIR99021, is lower than a method of making sensor neurons that fails make mechanoreceptors, and optionally fails to make nociceptors, mechanoreceptors, and/or proprioceptors are in ratios similar to those found in the dorsal root ganglia.

For example, in the experiments below, prior to differentiation, plates were coated with Geltrex at 1:100 dilution and stored at 4° C. overnight, or vitronectin. The next day, hPSCs were harvested as using EDTA for 15 min and plated at a density of 200,000 cells/cm2. On days 0 (day of plating) to 1 of the differentiation, cultures were fed with Essential 6 Medium containing 10 µM of TGFβ/Activin-Nodal signaling inhibitor SB431542, 1 ng/mL BMP4, 300 nM Wnt signaling activator CHIR99021, and 10 μM Y-27632. On day 2, NCC D2+ media was made with Essential 6 Medium containing 10 μM SB431542 and 1.5 μM or 0.75 μM CHIR99021. For SN induction, cells were maintained in D2-12 media containing 10 μM SB431542, 0.75 μM CHIR99021, 2.5 μM of FGFR inhibitor SU5402 and 2.5 μM of Notch inhibitor DAPT. Cells were fed every 48 h between day 2 and 12.

The methods typically include a step of replating. Neural crest cells (NCCs) could be pushed towards SNs by replating them on day 12 in a combination of SN-favoring growth factors (FIG. 1C) (Chambers, et al., Nat. Biotechnol. 30, 715-720 (2012), which is specifically incorporated by reference herein in its entirety), with the addition of DAPT (day 12-20), which reduces the number of SOX10+ progenitor cells and enriches the purity of the culture. Thus, in some embodiments, replating is on culture days 10, 11, 12, 13, 14 or 15, optionally in combination with SN-favoring growth factors. In the experiments below, on day 12, sensory neuron cultures were replated at a density of 250,000 cells/cm$^2$ onto plates coated with 15 μg/ml poly-L-ornithine hydrobromide and 2 μg/ml mouse-laminin-1, and 2 μg/ml human fibronectin (PO/LM/FN). Cells were dissociated with Accutase for 20 min, washed with PBS and resuspended in Sensory Neuron Media: Neurobasal media containing N2 supplement, B-27 supplement, 2 mM L-glutamine, 20 ng/ml each of GDNF, BDNF, 25 ng/ml NGF, 600 ng/ml of laminin-1, 600 ng/ml fibronectin, 1 μM DAPT and 0.125 μM retinoic acid. 20 ng/ml NT-3 was added where indicated. Cells were fed every 2-3 days through D20. On day 20, DAPT was removed and cells were fed every 3-4 days.

It was also found that SNs can be replated anytime between day 16 and day 50 and form a dense network 20 days post-replating. The experiments below, this late-replating of sensory neuron cultures was onto plates coated with 15 μg/ml poly-L-ornithine hydrobromide, 2 μg/ml of mouse-laminin-1 and 2 μg/ml human fibronectin. To replate, cells were dissociated with Accutase (Innovative Cell Technologies Inc., 84 #AT-104) for 45 min, washed once with PBS and resuspended in Sensory Neuron Media Cells with a p1000. SNs were then seeded onto the new plates at a density of 250,000 cells/cm2. Cells were fed every 2-3 days through day 20 or every 3-4 days afterwards.

Sequential culture of hESCs resulted in decreased NCC and SN differentiation efficiency over time, and thus is avoided in some embodiments.

Additionally or alternatively, this limitation could be overcome using the CryoPause method (Wong, et al., Stem Cell Reports 9, 355-365 (2017)).

It was also discovered that the cells could be frozen at the NCC stage (e.g., day 12).

In some embodiments, the method utilizes chemically defined conditions in monolayer culture to generate a combination of nociceptors, mechanoreceptors, proprioceptors.

In some embodiments, the method generates SN cells out of 60-70% of the cells.

In some embodiments, nociceptors, mechanoreceptors, and/or proprioceptors are in ratios similar to those found in the dorsal root ganglia. In some embodiments, the starting stem cells are ESC or iPSC.

In some embodiments, the neurons show neuron activity on day 25.

C. Enhancing Preparation and Isolation of Subtypes

In some embodiments, the method includes steps to drive the mixed SN population to a particular subtype(s), and/or includes a subtype(s) isolation step such as FACS or immunopanning.

Figure 3B:
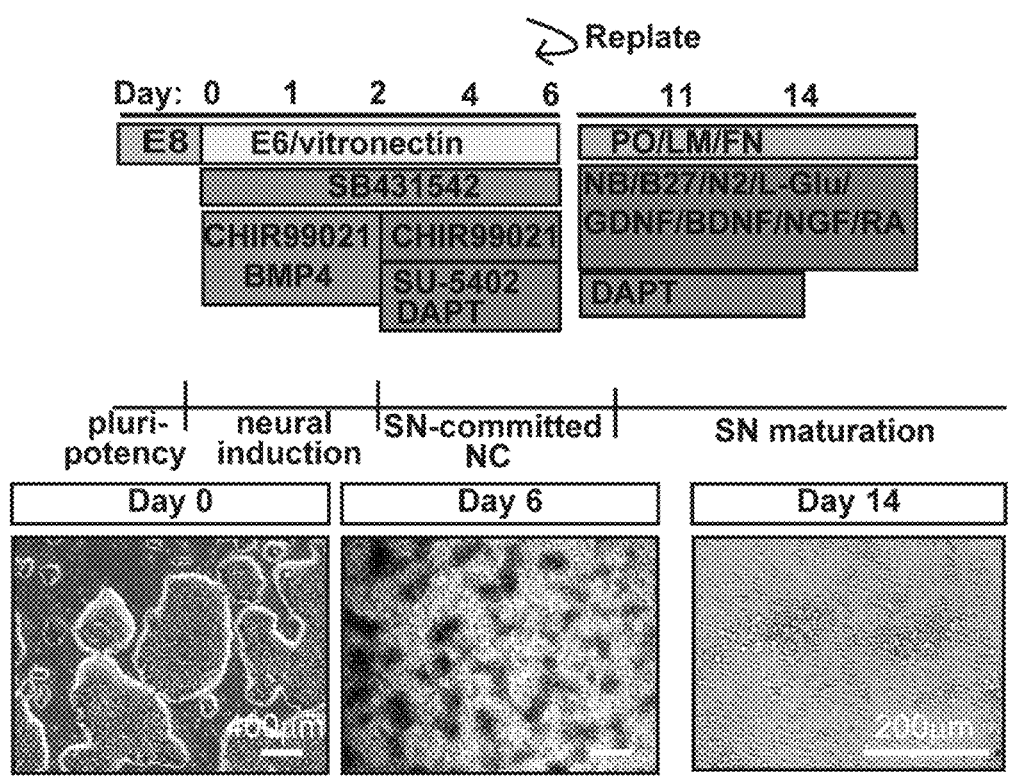
Figure 3C:
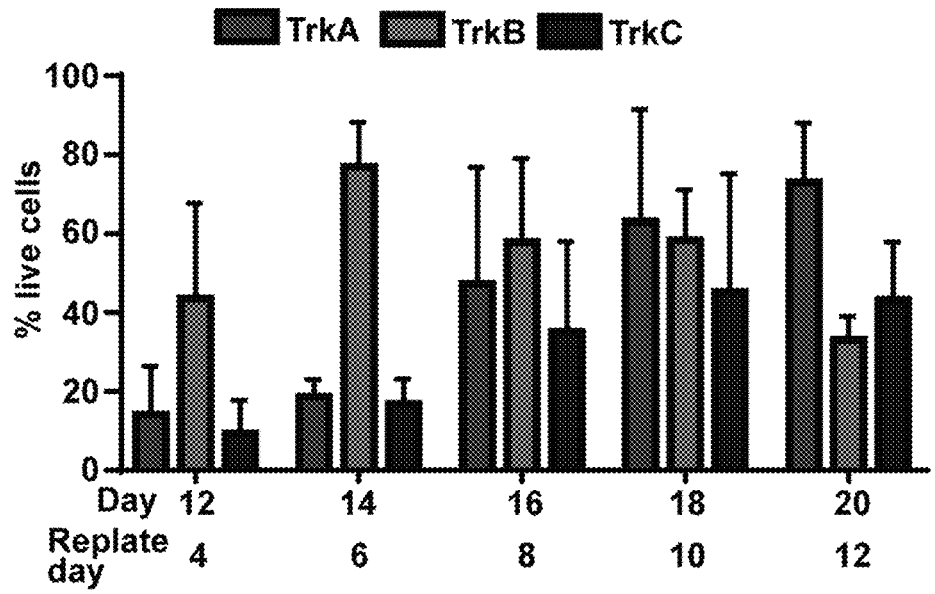

For example, in the experiments below, the SN-specified NCCs were replated at day 4, 6, 8, 10, 12 and TRK expression was assessed by FACS 8 days later (FIG. 3C). A dramatic enrichment (80%) of TRKB+ mechanoreceptors, when the replate was done at day 6, supporting the belief that this caught the first wave of SN development. Thus, in some embodiments, methods of making and enriching for mechanoreceptors include a replating at any one of days 4-12, preferably between days 4-8, most preferably on or about days 5, 6, or 7.

The experiments also show that nociceptors could be generated at ~90%, proprioceptors at ~38% by FACS and/or Immunopanning.

Immunopanning (Sloan, et al., Neuron 95, 779-790.e6 (2017), specifically incorporated by reference herein in its entirety) is a gentle antibody-based purification technique that can be used to segregate the different SN subtypes. This method allows the binding of specific cells from a mix to a dish pre-coated with antibodies against cell surface proteins. The cells of interest attach to the antibody and the following wash and dissociation steps are much gentler compared to FACS. Results below show that TRKA+ nociceptors, TRKB+ mechanoreceptors and 192 TRKC+ proprioceptors could be isolated from bulk day 25 SN cultures. Suitable cells markers that can be targeted by antibodies for immunopanning are discussed elsewhere herein.

In some embodiments any one or more of the reagents and time points to methods as exemplified in the experiments below are varied up or down by any integer value within and including 15 times more or less, or any specific range there between, of the utilized concentration/amount.

In preferred embodiments, differentiation is a chemically defined monolayer culture, which bypasses the need to generate neurospheres (Alshawaf, et al., Scientific Reports 8, 603 (2018), Boisvert, et al., Sci Rep 5, 16821 (2015), Schrenk-Siemens, et al., Nat. Neurosci. 18, 10-550 16 (2015), Young, et al., Mol Ther 22, 1530-1543 (2014)) and optionally, but preferably with only one replating step (e.g., day 12). Thus, in some embodiments, the method does not include the generation of neurospheres.

Typically the results differentiated SNs are functional. Function can be used using any suitable method, including those discussed in the experiments below.

III. Cell Populations and Compositions Thereof

A. Cell Populations

Cells prepared according the disclosed methods are also provided. Thus, the presently disclosed subject matter provides compositions including a population of differentiated sensory neurons or a subtype(s) thereof such as nociceptors, mechanoreceptors, and/or proprioceptors produced by the in vitro differentiation methods described herein. In certain non-limiting embodiments, the differentiated cells are prepared from embryonic pluripotent stem cells, such as human embryonic pluripotent stem cells. In certain non-limiting embodiments, the differentiated cells are prepared from induced pluripotent stem cells, such as induced human pluripotent stem cells.

Compositions including a population of in vitro differentiated cells are also provided. In some embodiments, at least about 50%, (e.g., at least about 55%, at least about 60%, at least about 65%, at least about 70%, at least about 75%, at least about 80%, at least about 85%, at least about 90%, at least about 95%, at least about 99%, or at least about 99.5%) of the population of cells express one or more markers of the desired differentiated cell population, and/or lack one or more markers of pluripotent cells and/or an undesired differentiated cell population.

In some embodiments the desired differentiated cell type is sensory neurons, or one more sensory neuron subtypes such as nociceptors, mechanoreceptors and/or proprioceptors. In some embodiments the undesired cell type is stem cells and/or other non-sensory neuron differentiated cells.

Markers of pluripotent stem cells, partially differentiated and differentiated sensory neurons such as nociceptors, mechanoreceptors and/or proprioceptors that can be used to distinguish cells types are discussed herein, such as in the Examples below, and are known in the art.

See, e.g., U.S. Published Application No. 2019/0093074 which is specifically incorporated by reference herein in its entirety.

Non-limiting examples of peripheral sensory neuron markers include Brn3A, peripherin, and ISL1. Non-limiting examples of proprioceptor markers include TrkC, RUNX3, CDHL1, ETV1, and ETV4. Non-limiting examples of nociceptor markers include TrkA and RUNX1. Non-limiting examples of mechanoreceptor markers include TrkB and RET.

Non-limiting examples of stem cell markers include OCT4, NANOG, SOX2, LIN28, SSEA4 and SSEA3.

Non-limiting examples of central nervous system (CNS) markers include PAX6, NESTIN, Vimentin, FOXG1, SOX2, TBR1, TBR2 and SOX1. Non-limiting examples of neuronal cell markers include TUJ1, MAP2, NFH, BRN3A, ISL1, TH, ASCL1, CHAT, PHOX2B, PHOX2A, TRKA, TRKB, TRKC, 5HT, GABA, NOS, SST, TH, CHAT, DBH, Substance P, VIP, NPY, GnRH, and CGRP. Non-limiting examples of mesenchymal precursor markers are SMA, Vimentin, HLA-ABC, CD105, CD90 and CD73. Non-limiting examples of Cranial Neural Crest (CNC) markers include PAX6, NESTIN, Vimentin, FOXG1, SOX2, TBR1, TBR2 and SOX1. Non-limiting examples of Melanocyte-competent Neural Crest (MNC) markers include PAX6, NESTIN, Vimentin, FOXG1, SOX2, TBR1, TBR2 and SOX1.

Other exemplary markers are discussed in the Examples below and can also be used. For example, nociceptors expressed SST, PLXNC1 and Substance P (SubP) (FIGS. 2A-2D). Expression of the members of the transient receptor (TRP) family TRPV1 and TRPV2 (expressed in medium-to large-diameter nociceptors), the temperature sensitive receptor TRPM8, and the cold-activated receptor TRPA1 (FIG. 2A) were also found. Finally, expression of SCN8A-11A genes (encode Na+ channels Nav1.6-9) and the ATP-activated receptor P2X3 were also investigated.

Similarly, mechanoreceptors expressed the mechanically-activated K+ channels TREK-1 (KCNK2) and TRAAK (KCNK4), the acid-sensing ion channels (ASIC1-3) expressed in the Meissner corpuscles and Merkel cells, NF200 (expressed in myelinated A-β fiber neurons), PIEZO2 (expressed in C-low threshold mechanoreceptors), NECAB2, and FAM19A1 (expressed in low threshold mechanoreceptors).

Figure 2A:
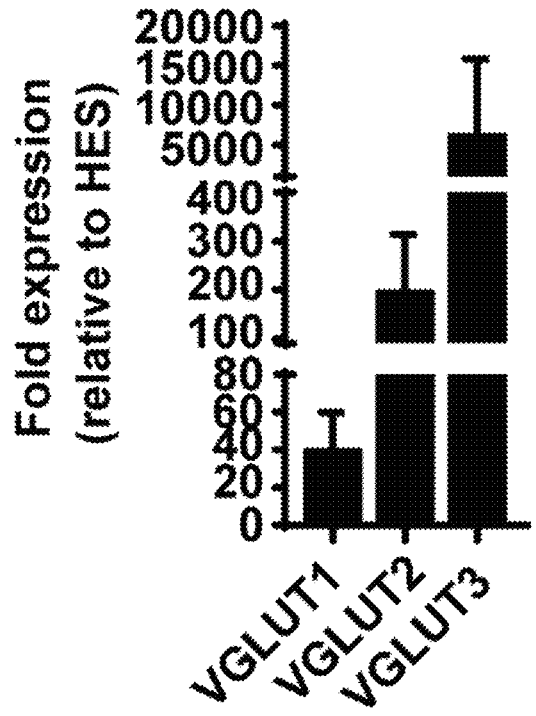
Figure 2B:
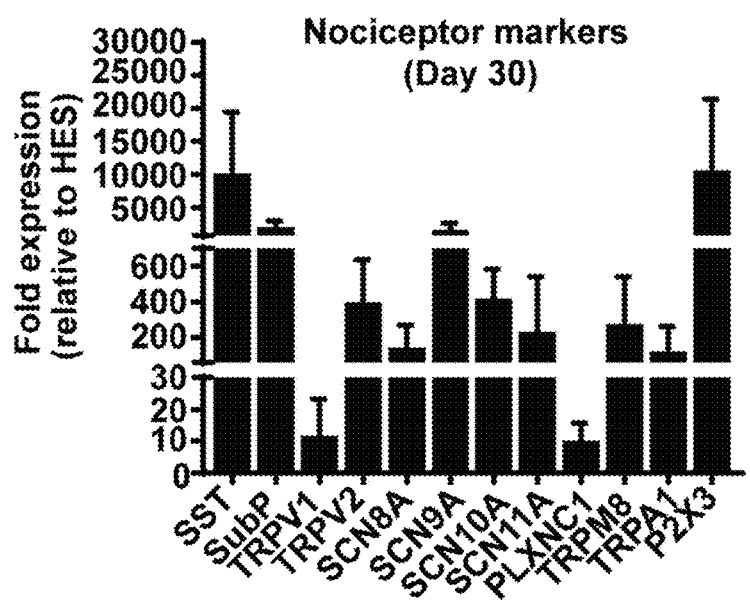
Figure 2C:
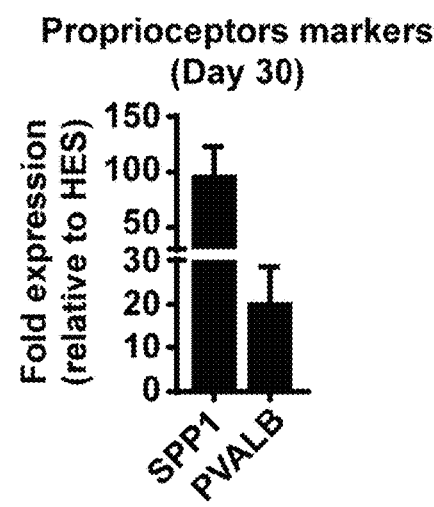
Figure 2D:
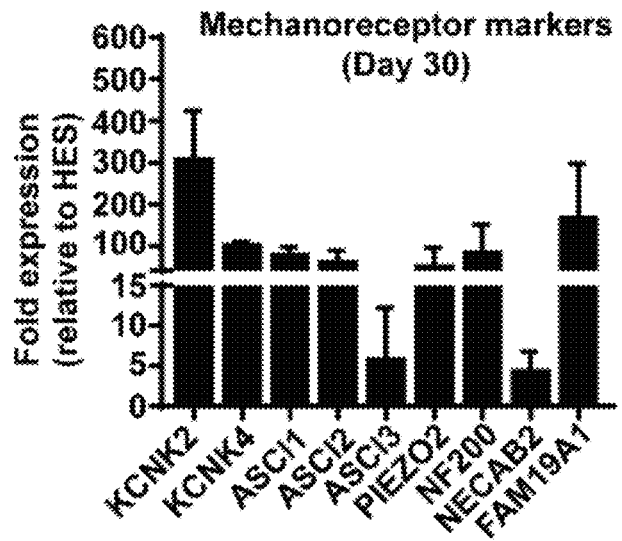

Proprioceptors expressed SPP1 and Parvalbumin (PVALB). Protein expression of the nociceptor-related marker calcitonin-gene related protein (CGRP) and SubP was also confirmed on day 50 by immunofluorescence (FIGS. 2B-2D).

In some embodiments, less than about 50% (e.g., less than about 45%, less than about 40%, less than about 35%, less than about 30%, less than about 25%, less than about 20%, less than about 15%, less than about 10%, less than about 5%, less than about 4%, less than about 3%, less than about 2%, less than about 1%, less than about 0.5%, or less than about 0.1%) of the population of cells express one or more markers of pluripotent cells and/or an undesired differentiated cell population.

B. Genetically Modified Cells

In some embodiments, the disclosed cells do not contain any gene or genetic modification. Additionally or alternatively, the cells can also be free from transfection with nucleic acid constructs. For example, as exemplified below, the differentiation programs described herein can be carried out without gene modification or transgene expression.

However, in some embodiments, the precursor stem cells and or the differentiated cells have been genetically modified and/or include one or more nucleic acid expression constructs. Gene modifications typically refer to modification of the cell's genome can include induced by any suitable means, e.g., triplex-forming molecules, pseudocomplementary oligonucleotides, CRISPR/Cas, zinc finger nucleases, TALENs, viral mediated integration, etc. These technologies are known in the art can be used to make modifications to the cells ranging from point mutations to deletions and insertions of e.g., expression constructs. Additional or alternative, the cells may optionally be transfected with transient or permanently nucleic acid expression constructs in the form of e.g., mRNA, viral vectors, plasmids, and other extrachromosomal means of gene expression. Such genetic modifications and expression constructs can be used for a variety of purposes including, but not limited to, facilitating or enhancing preparation of the precursor (e.g., stem) cells, preparation of the differentiated cells (e.g., sensor neurons), and/or for gene therapy.

In particularly preferred embodiments containing a genetic modification or extrachromosomal expression construct, the cells are enhanced for use in gene therapy applications. Gene therapy is a technique that modifies a person's genes to treat or cure disease. Gene therapies can work by several mechanisms, for example, (1) replacing a disease-causing gene with a healthy copy of the gene; (2) inactivating a disease-causing gene that is not functioning properly; or (3) introducing a new or modified gene into the body to help treat a disease. For example, in some embodiments, the cells are used to a treat a disease, such a genetic disorder, that includes reduced expression of a wildtype protein and/or expression of mutant protein. Such cells can be modified to, for example, reverse a detrimental genetic mutation and/or express or overexpress a compensatory protein.

Thus, in some embodiments, cells prepared according to the disclosed methods are infected, transfected or otherwise modified to express an expression construct. For example, constructs can be inserted into vectors for expression in cells. As used herein, a "vector" is a replicon, such as a plasmid, phage, or cosmid, etc., into which another DNA segment may be inserted so as to bring about the replication of the inserted segment. Vectors can be expression vectors. An "expression vector" is a vector that includes one or more expression control sequences, and an "expression control sequence" is a DNA sequence that controls and regulates the transcription and/or translation of another DNA sequence. Nucleic acids in vectors can be operably linked to one or more expression control sequences. As used herein, "operably linked" means incorporated into a genetic construct so that expression control sequences effectively control expression of a coding sequence of interest. Examples of expression control sequences include promoters, enhancers, and transcription terminating regions. A promoter is an expression control sequence composed of a region of a DNA molecule, typically within 100 nucleotides upstream of the point at which transcription starts (generally near the initiation site for RNA polymerase II). To bring a coding sequence under the control of a promoter, it is necessary to position the translation initiation site of the translational reading frame of the polypeptide between one and about fifty nucleotides downstream of the promoter. Enhancers provide expression specificity in terms of time, location, and level. Unlike promoters, enhancers can function when located at various distances from the transcription site. An enhancer also can be located downstream from the transcription initiation site. A coding sequence is "operably linked" and "under the control" of expression control sequences in a cell when RNA polymerase is able to transcribe the coding sequence into mRNA, which then can be translated into the protein encoded by the coding sequence.

Suitable expression vectors include, without limitation, plasmids and viral vectors derived from, for example, herpes viruses, cytomegalo virus, retroviruses, vaccinia viruses, adenoviruses, and adeno-associated viruses. Numerous vectors and expression systems are commercially available from such corporations as Novagen (Madison, Wis.), Clontech (Palo Alto, CA), Stratagene (La Jolla, CA), and Invitrogen Life Technologies (Carlsbad, CA).

C. Compositions Including Cell Populations

Compositions including cell populations made according to the disclosed methods are also provided. In certain non-limiting embodiments, the composition includes a biocompatible scaffold or matrix, for example, a biocompatible three-dimensional scaffold that facilitates tissue regeneration when the cells are implanted or grafted to a subject. In certain non-limiting embodiments, the biocompatible scaffold comprises extracellular matrix material, synthetic polymers, cytokines, collagen, polypeptides or proteins, polysaccharides including fibronectin, laminin, keratin, fibrin, fibrinogen, hyaluronic acid, heparin sulfate, chondroitin sulfate, agarose or gelatin, and/or hydrogel. (See, e.g., U.S. Publication Nos. 2015/0159135, 2011/0296542, 2009/0123433, and 2008/0268019, the contents of each of which are incorporated by reference in their entireties).

In certain embodiments, the composition is a pharmaceutical composition that comprises a pharmaceutically acceptable carrier, excipient, diluent or a combination thereof. In certain embodiments, the compositions can be used to treat or prevent a sensory neuron disorder. In certain embodiments, the compositions can be used for preventing and/or treating a disorder of nociceptors, mechanoreceptors and/or proprioceptors neurons and/or a neurodegenerative disease or disorder, e.g., Friedreich's Ataxia or Parkinson's disease.

The compositions can be provided as sterile liquid preparations, e.g., isotonic aqueous solutions, suspensions, emulsions, dispersions, or viscous compositions, which may be buffered to a selected pH. Liquid preparations are normally easier to prepare than gels, other viscous compositions, and solid compositions. Additionally, liquid compositions are somewhat more convenient to administer, especially by injection. Viscous compositions, on the other hand, can be formulated within the appropriate viscosity range to provide longer contact periods with specific tissues. Liquid or viscous compositions can comprise carriers, which can be a solvent or dispersing medium containing, for example, water, saline, phosphate buffered saline, polyol (for example, glycerol, propylene glycol, liquid polyethylene glycol, and the like) and suitable mixtures thereof. Sterile injectable solutions can be prepared by incorporating the compositions of the presently disclosed subject matter, in the required amount of the appropriate solvent with various amounts of the other ingredients, as desired. Such compositions may be in admixture with a suitable carrier, diluent, or excipient such as sterile water, physiological saline, glucose, dextrose, or the like. The compositions can also be lyophilized. The compositions can contain auxiliary substances such as wetting, dispersing, or emulsifying agents (e.g., methylcellulose), pH buffering agents, gelling or viscosity enhancing additives, preservatives, colors, and the like, depending upon the route of administration and the preparation desired. Standard texts, such as "REMINGTON'S PHARMACEUTICAL SCIENCE", 17th edition, 1985, incorporated herein by reference, may be consulted to prepare suitable preparations, without undue experimentation.

Various additives which enhance the stability and sterility of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. Prolonged absorption of the injectable pharmaceutical form can be brought about by the use of agents delaying absorption, for example, aluminum monostearate and gelatin. According to the presently disclosed subject matter, however, any vehicle, diluent, or additive used would have to be compatible with the presently disclosed cells.

Viscosity of the compositions, if desired, can be maintained at the selected level using a pharmaceutically acceptable thickening agent. Methylcellulose can be used because it is readily and economically available and is easy to work with. Other suitable thickening agents include, for example, xanthan gum, carboxymethyl cellulose, hydroxypropyl cellulose, carbomer, and the like. The concentration of the thickener can depend upon the agent selected. The important point is to use an amount that will achieve the selected viscosity. Obviously, the choice of suitable carriers and other additives will depend on the exact route of administration and the nature of the particular dosage form, e.g., liquid dosage form (e.g., whether the composition is to be formulated into a solution, a suspension, gel or another liquid form, such as a time release form or liquid-filled form).

Compositions should be selected to be chemically inert and will not affect the viability or efficacy of the presently disclosed cells. This will present no problem to those skilled in chemical and pharmaceutical principles, or problems can be readily avoided by reference to standard texts or by simple experiments, from this disclosure and the documents cited herein.

IV. Methods of Use

Methods of using the disclosed differentiated cells and compositions thereof are also provided. The methods include investigation of disease etiology, treatment of diseased subjects, and testing of compounds for e.g., therapeutic or toxic effect.

A. Methods of Treatment

In certain embodiments the in vitro differentiated cells and/or a composition thereof can be used for preventing and/or treating a disorder of sensory neurons. Such methods of preventing and/or treating a disorder of neurons and/or a neurodegenerative disorder can include administering to a subject in need thereof a therapeutically effective amount of the presently disclosed differentiated cells or a composition thereof.

The cells or compositions thereof can be administered or provided systemically or locally to a subject for preventing and/or treating the disease or disorder. In certain embodiments, cells or composition are directly injected into an organ of interest (e.g., an organ affected by a disorder of neurons and/or a neurodegenerative disorder).

The cells and compositions thereof can be administered in any physiologically acceptable vehicle. Pharmaceutical compositions cell or a composition thereof and a pharmaceutically acceptable carrier are also provided. In some embodiments, the cells or compositions are administered via localized orthotropic (OT) injection, local application, systemic injection, intravenous injection, or parenteral administration.

The cells or a composition thereof can be administered to a subject in a therapeutically effective amount. A "therapeutically effective amount" is an amount sufficient to affect a beneficial or desired clinical result upon treatment. A therapeutically effective amount can be administered to a subject in one or more doses. In terms of treatment, a therapeutically effective amount is an amount that is sufficient to palliate, ameliorate, stabilize, reverse or slow the progression of the disorder of neurons and/or neurodegenerative disorder, or otherwise reduce the pathological consequences of the disorder of neurons and/or neurodegenerative disorder. The therapeutically effective amount is generally determined by the physician on a case-by-case basis and is within the skill of one in the art. Several factors are typically taken into account when determining an appropriate dosage to achieve a therapeutically effective amount. These factors include age, sex and weight of the subject, the condition being treated, the severity of the condition and the form and effective concentration of the cells administered.

The quantity of cells to be administered will vary for the subject being treated. In certain embodiments, from about $1\times10^4$ to about $1\times10^{10}$, from about $1\times10^4$ to about $1\times10^5$, from about $1\times10^5$ to about $1\times10^9$, from about $1\times10^5$ to about $1\times10^6$, from about $1\times10^5$ to about $1\times10^7$, from about $1\times10^6$ to about $1\times10^7$, from about $1\times10^6$ to about $1\times10^8$, from about $1\times10^7$ to about $1\times10^8$, from about $1\times10^8$ to about $1\times10^9$, from about $1\times10^8$ to about $1\times10^{10}$, or from about $1\times10^9$ to about $1\times10^{10}$ the presently disclosed cells are administered to a subject. The precise determination of what would be considered a therapeutically effective dose may be based on factors individual to each subject, including their size, age, sex, weight, and condition of the particular subject. Dosages can be readily ascertained by those skilled in the art from this disclosure and the knowledge in the art.

In some embodiments, the cells are transiently or genetically modified as discussed above. Such cells can serve as a combination of both cell and gene therapy. The appropriate gene modification and/or recombinant expression construct can be selected by the practitioner based on the disease or disorder to be treated. For example, in some embodiments the cells are modified to enhance treatment of a monogenic disorder. Monogenic disorders (monogenic traits) are caused by variation in a single gene and are typically recognized by their striking familial inheritance patterns. In such embodiments, the genetic modification may reverse or correct or otherwise compensate for the mutated gene by, for example, expressing a wildtype copy of the mutant gene.

A non-limiting example is Friedreich's Ataxia. Friedreich's ataxia is an inherited disorder that affects some of the body's nerves. It is caused by a defect (mutation) in a gene labeled FXN, which carries the genetic code for a protein called frataxin. Thus, in some embodiments, the cells are genetical modified to express one or more wildtype copies of frataxin, e.g., by having one or more endogenous gene and/or heterologous expression constructs that encode and express wildtype frataxin (e.g., an active copy of the FXN gene).

Another non-limiting example is Familial Dysautonomia (FD). FD is a monogenetic disorder that is caused by a homozygous point mutation in the ELP1 gene. This leads to missplicing of the elongator complex protein 1 (ELP1) protein. The mutant protein is degraded, and patients thus have dramatically reduced levels of ELP1 protein. This is particularly prevalent in sensory and sympathetic tissues. Thus, in some embodiments, the cells are genetical modified to express one or more wildtype copies of ELP1 protein, e.g., by having one or more endogenous gene and/or heterologous expression constructs that encode and express wildtype ELP1 protein (e.g., an active copy of the ELP1 gene). Accordingly, for example, ELP1-gene delivery into hPSC-derived SNs and transplanted into the DRG of patients may be used as a therapy for FD.

B. Drug Screening

The disclosed cells and compositions thereof are useful to investigate the activity or applicability of one or more test compounds to treat or alleviate one or more symptoms of a neuronal or neurodegenerative disease or disorder.

In a typical embodiment, cells are cultured under conditions suitable to induce differentiation of the desired cell population as disclosed herein. In some embodiments, the cells are isolated from a diseased subject, or healthy cells are treated with a disease-inducing compound, to form a diseased, dysfunctional, or a defective cell model. One or more test compounds can be applied to cultured differentiated cells and evaluated for the ability to treat one or more symptoms of the diseased, dysfunctional, or defective cells. The symptom or symptoms can be specific to the disease state being studied, or can be of a generally nature.

In some embodiments, healthy cells are utilized, and compounds are tested for toxicity and/or the ability to further improve one or more wildtype functions.

Physiological, phenotypic, morphological, or molecular symptoms and other markers of the cells can be monitored over time.

C. Diseases and Disorders

Diseases and disorders that can be the subject of the disclosed methods include those that effect sensory neurons and may be neurodevelopmental and/or neurodegenerative. In some embodiments the disease or disorder is a peripheral nervous system (PNS) disease or disorder.

Exemplary PNS diseases and disorders include, but are not limited to, Accessory nerve disorder, Alcoholic polyneuropathy, Anesthesia dolorosa, Anti-MAG peripheral neuropathy, Autoimmune autonomic ganglionopathy, Autonomic diseases, Autonomic dysreflexia, Autonomic neuropathy, Axillary nerve dysfunction, Axillary nerve palsy, Charcot-Marie-Tooth disease, Charcot-Marie-Tooth disease classifications, Chemotherapy-induced peripheral neuropathy, Chronic solvent-induced encephalopathy, CMV polyradiculomyelopathy, Congenital insensitivity to pain with anhidrosis, Denervation, Diabetic neuropathy, Dysautonomia, Erythromelalgia, Facial nerve paralysis, Familial dysautonomia (FD), Friedreich's Ataxia, Guillain-Barré syndrome, Hereditary sensory and autonomic neuropathy, Hereditary sensory and autonomic neuropathy type I, Horner's syndrome, Multiple system atrophy, Nerve compression syndrome, Nerve injury, Neurapraxia, Neuritis, Orthostatic hypotension, Orthostatic intolerance, Paroxysmal sympathetic hyperactivity, Peripheral mononeuropathy, Peripheral neuropathy, Piriformis syndrome, Plexopathy, Polyneuropathy, Postural orthostatic tachycardia syndrome, Primary autonomic failure, Pronator teres syndrome, Proximal diabetic neuropathy, Pudendal nerve entrapment, Pure autonomic failure, Quadrilateral space syndrome, Radial nerve dysfunction, Radial neuropathy, Radiation-induced lumbar plexopathy, Radiculopathy, Sciatica, Small fiber peripheral neuropathy, Thoracic outlet syndrome, Ulnar neuropathy, Vasculitic neuropathy, Villaret's syndrome, Wartenberg's syndrome, and Winged scapula.

Exemplary neurodegenerative diseases include, but are not limited to, amyotrophic lateral sclerosis (ALS), Huntington's disease (HD), and muscular dystrophies, problems with the way the nervous system develops, such as spina bifida, degenerative diseases, where nerve cells are damaged or die, such as Parkinson's disease (PD) and PD-related disorders, meningitis, prion diseases such as Creutzfeldt-Jakob Disease, corticobasal degeneration, frontotemporal dementia, cognitive impairment including mild cognitive impairment and HIV-related cognitive impairment, motor neuron diseases (MND), spinocerebellar ataxia (SCA), spinal muscular atrophy (SMA), Friedreich's Ataxia, Lewy Body Disease, Alpers' Disease, Batten Disease, Cerebro-Oculo-Facio-Skeletal Syndrome, Corticobasal Degeneration, Gerstmann-Straussler-Scheinker Disease, Kuru, Leigh's Disease, monomelic amyotrophy, multiple system atrophy, multiple system atrophy with orthostatic hypotension (Shy-Drager Syndrome), Multiple Sclerosis (MS), neurodegeneration (e.g., with brain iron accumulation), opsoclonus myoclonus, posterior cortical atrophy, primary progressive aphasia, progressive supranuclear palsy, vascular dementia, progressive multifocal leukoencephalopathy, dementia with Lewy Bodies, lacunar syndromes, hydrocephalus, Wernicke-Korsakoff's syndrome, post-encephalitic dementia, cancer and chemotherapy-associated cognitive impairment and dementia, and depression-induced dementia, Guillain-Barré syndrome, and pseudodementia.

The invention can be further understood by the following numbered paragraphs:

1. A method of making sensory neurons comprising culturing of stem cells in monolayer in chemically-defined differentiation media.
2. The method of paragraph 1, wherein the cells are cultured on a vitronectin substrate.
3. The method of paragraphs 1 or 2, wherein differentiation is initiated the same day as seeding the stem cells.
4. The method of any one of paragraphs 1-3, wherein the differentiation media comprises one or more of CHIR99021, FGFR/VEGFR inhibition (SU-5402) and Notch inhibition (DAPT).
5. The method of paragraph 4, wherein CHIR99021 is about 300 nM.
6. The method of any one of paragraphs 1-5, further comprising one or more replatings.
7. The method of paragraph 6, comprising a replating on or about day 12.
8. The method of any one of paragraphs 1-7, wherein the method induces differentiation of about 60-70% of the cell into sensory neurons.
9. The method of any one of paragraphs 1-8, wherein the sensory neurons comprise nociceptors, mechanoreceptors, and/or proprioceptors.
10. The method of any one of paragraphs 1-8, wherein the nociceptors, mechanoreceptors, and/or proprioceptors are in ratios similar to those found in the dorsal root ganglia.
11. The method of any one of paragraphs 9-10 further comprising enriching the nociceptors, mechanoreceptors, and/or proprioceptors.
12. The method of paragraph 11, wherein the enriching comprising replating at day six to increase generation mechanoreceptors.
13. The method of paragraphs 11 or 12 comprising FACS and/or immunopanning to enrich one or more of nociceptors, mechanoreceptors, and/or proprioceptors.
14. The method of any one of paragraphs 1-13 comprising isolating sensory neurons, nociceptors, mechanoreceptors, proprioceptors, or a combination thereof from other cells in the culture.
15. A population of cells formed according to the method of any one of paragraphs 1-13.
16. A composition comprising the population of cells according to paragraph 15.
17. The composition of paragraph 16 comprising a matrix or substrate for the cells.
18. The composition of paragraphs 16 or 17 in a pharmaceutical composition comprising a pharmaceutically acceptable carrier.
19. A method of treating a subject in need thereof, optionally wherein the subject has a peripheral neuron disorder or a neurodegenerative disease comprising administering the subject an effective amount of the cells or paragraph 15 of the composition of any one of paragraphs 16-18.
20. A method of screening for compounds comprising contacting cells of paragraph 15 or the composition of any one of paragraphs 16-18 with one or more compounds and selecting the compound if it increases one or more functions of the cells or reduces one or more functions of the cells.
21. Any of the foregoing paragraphs wherein the cells are embryonic stem cells or induced pluripotent stem cells.
22. A method of inducing sensory neurons according to the description, experiments, figures, or other disclosure herein, or any combination thereof.
23. Cells formed according to the method of paragraph 22.
24. A composition comprising the cells of paragraph 23, optionally wherein the composition matrix or substrate for the cells and/or is a pharmaceutical composition comprising a pharmaceutically acceptable carrier.
25. A method of treating a subject in need thereof, optionally wherein the subject has a peripheral neuron disorder or a neurodegenerative disease comprising administering the subject an effective amount of the cells of paragraph 23 or the composition of paragraph 24.
26. A method of screening for compounds comprising contacting cells of paragraph 23 or the composition of paragraph 24 with one or more compounds and selecting the compound if it increases one or more functions of the cells or reduces one or more functions of the cells.

EXAMPLES

Saito-Diaz, et al., "Derivation of Peripheral Nociceptive, Mechanoreceptive, and Proprioceptive Sensory Neurons from the same Culture of Human Pluripotent Stem Cells," *Stem Cell Reports,* 16(3): 446-457 (2021), including the 16 page of Supplemental Information associated therewith, doi.org/10.1016/j.stemcr.2021.01.001, is specifically incorporated by reference in its entirety.

Example 1: A Method for SN Generation Mimicking the DRG Neuronal Composition

Materials and Methods

Reagents, companies and catalog #, cell lines, antibodies, and primers are listed in Tables 1-3 and the Additional Materials section below.

hPSC and iPSC Maintenance

Human embryonic stem cells (WA-09, WiCell) were grown at 37° C./5% CO2 and fed daily with Essential 8 Medium+Supplement on dishes coated with vitronectin (5 μg/mL, 1 h at RT). For splitting, H9 colonies were washed with 1×PBS and treated with 0.5 mM EDTA, in PBS with 3.08 M NaCl for 2 min at 37° C. Cells were resuspended in Supplemented E8 and split at a ratio of 1:10. Control and FD iPSCs were previously characterized (Zeltner, et al., *Nat. Med.* 22, 1421-1427 (2016)) and maintained with the same conditions.

Neural Crest and Sensory Neuron Culture Conditions

Prior to differentiation, plates were coated with Geltrex at 1:100 dilution and stored at 4° C. overnight, or vitronectin. The next day, hPSCs were harvested as using EDTA for 15 min and plated at a density of 200,000 cells/cm2. On days 0 (day of plating) to 1 of the differentiation, cultures were fed with Essential 6 Medium containing 10 μM SB431542, 1 ng/mL BMP4, 300 nM CHIR99021, and 10 μM Y-27632. On day 2, NCC D2+ media was made with Essential 6 Medium containing 10 μM SB431542 and 1.5 μM or 0.75 μM CHIR99021. For SN induction, cells were maintained in D2-12 media containing 10 μM SB431542, 0.75 μM CHIR99021, 2.5 μM SU5402 and 2.5 μM DAPT. Cells were fed every 48 h between day 2 and 12.

On day 12, sensory neuron cultures were replated at a density of 250,000 cells/cm2 onto plates coated with 15 μg/ml poly-L-ornithine hydrobromide and 2 μg/ml mouse-laminin-1, and 2 μg/ml human fibronectin (PO/LM/FN). Cells were dissociated with Accutase for 20 min, washed with PBS and resuspended in Sensory Neuron Media: Neurobasal media containing N2 supplement, B-27 supplement, 2 mM L-glutamine, 20 ng/ml each of GDNF, BDNF, 25 ng/ml NGF, 600 ng/ml of laminin-1, 600 ng/ml fibronectin, 1 μM DAPT and 0.125 μM retinoic acid.

20 ng/ml NT-3 was added where indicated. Cells were fed every 2-3 days through D20. On day 20, DAPT was removed and cells were fed every 3-4 days.

Immunostaining

Adherent cultures from either 24- or 4-well plates were fixed with 4% paraformaldehyde for 20 mins at RT then washed twice in 1×PBS and stored in PBS at 4° C. Cells were permeabilized for 20 mins with PBS solution containing 1% BSA, 0.3% Triton-X, 3% goat or donkey serum and 0.01% sodium azide. Wells were stained with Permeabilization buffer without Triton-X, containing the primary antibodies overnight at 4° C. The cells were washed three times in 1×PBS and incubated for 1 h with secondary antibodies in antibody buffer. Cells were washed with PBS and incubated with DAPI (1:1,000 in PBS) for 5 minutes, washed with PBS and stored in the dark at 4° C. All imaging was done using the Lionheart FX fluorescence microscope (Biotek), and all image analysis and quantifications were done using IMAGEJ software. For quantifications, 5 different fields were imaged and quantified.

Gene Expression Analysis

Total RNA was isolated using Trizol reagent according to manufacturers' conditions and was resuspended in 20 μL RNase-free water. Concentration was measured on Nano-Drop One (Thermo Scientific). 1 μg of RNA was then converted to cDNA using iScript cDNA Synthesis kit according to manufacturer's instructions and diluted 1:100 in water. RT-qPCR reactions were run with 1 ul of cDNA and SYBR Green Supermix using a C1000 Touch Thermal Cycler CFX96 (BioRad). Cycling parameters were 95° C. for 5 min, 40 cycles of 95° C. for 5 sec and 60° C. for 10 seconds. Results were analyzed using the comparative CT method. GAPDH was used as a housekeeping gene (it was the most stably expressed among the 5 housekeeping genes tested). Graphs were generated on PRISM (GraphPad).

Flow Cytometry

Cells were dissociated with Accutase for 20 min and then washed in Flow buffer: DMEM 2% FBS and 1 mM L-glutamine. Cells were centrifuged at 200 g for 4 min and resuspended in cold PBS, they were counted and diluted to a concentration of 1×106 cells/100 μL and incubated for 20 min (CD49d) or 1 h (TRKA, B and C) with conjugated antibody. Cells were then washed twice in Flow buffer, and incubated with DAPI (1:1,000) in 300 μL of Flow buffer for 5 mins. Cells were filtered and transferred to a 96-well plate. Samples were run using a Cytoflex S (Beckman). All subsequent analysis was done using FlowJo.

Reproducibility

Biological repeats (N, min of 3 or otherwise indicated) represent individual differentiations that started from different splits or thaws of hPSCs. Differentiation was determined to be successful if it passed through specific checkpoints (FIG. 4A-4D), i.e. formation of NCC ridges by BF microscopy, high expression of SOX10 (≥100 fold compared to day 0) and BRN3A/TUJ1 expression by day 20. Reasons for unsuccessful differentiations are: initial seeding density below 200,000 cells/cm2 or multiple cell passages before differentiation.

Results

Figure 1B:
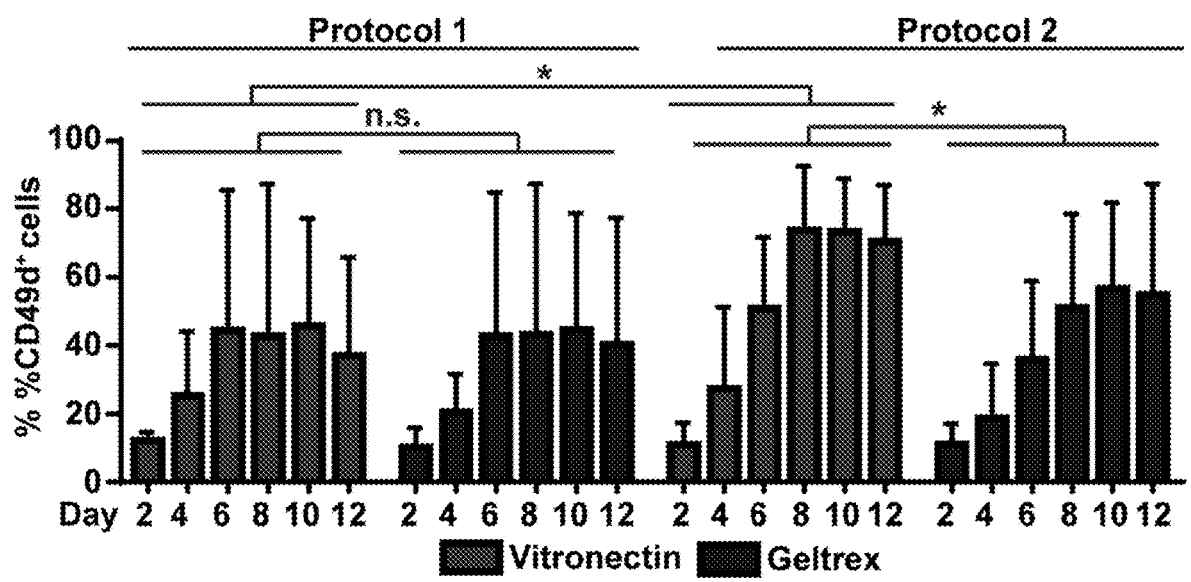

Since all DRG SNs are derived from NCCs, a first aim was to generate a protocol to derive NCCs efficiently. The WNT pathway is a key regulator of NCC development in vivo (Ji, et al., *Cells* 8, 1173 (2019)) and in generating NCCs from human PSCs (hPSCs) (Menendez, et al., *PNAS* 108, 19240-19245 (2011), Mica, et al., *Cell Rep* 3, 1140-1152 (2013)). Differentiation initiation timing, CHIR99021 concentrations (=WNT activation), and surface coatings (FIG. 1A) were tested, and it was discovered that (i) initiating the differentiation the day of seeding (rather than 24 h later), (ii) lowering the concentration of CHIR99021 and using vitronectin (VTN, rather than geltrex) resulted in dense NC 'ridges', ~80% NCCs, measured by expression of CD49D (FIG. 1B, which correlate with SOX10 (Fattahi, et al., *Nature* 531, 105-109 (2016)) and SOX10 robust expression.

Figure 5A:
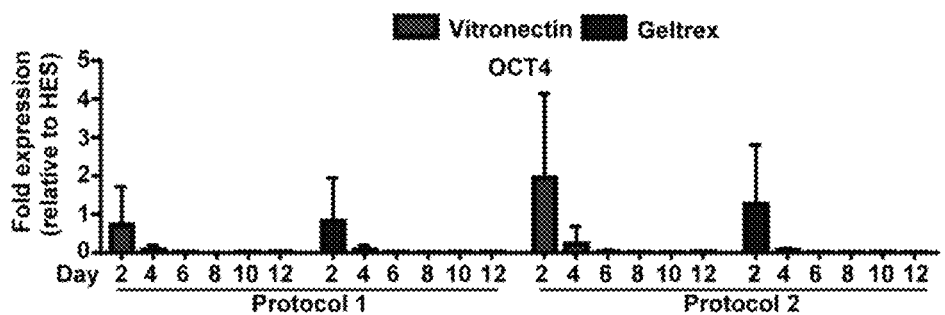
FIG. 5A-5J illustrate generation and characterization of hPSC-derived SNs (related to FIGS. 1A-1J).
Figure 5B:
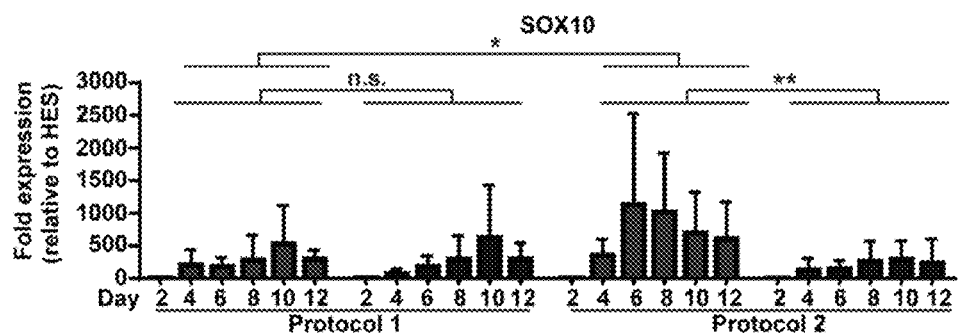
Figure 5C:
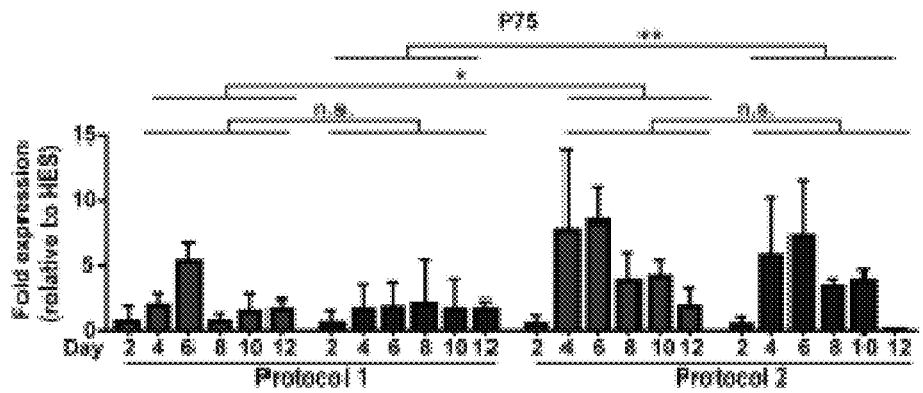

To confirm the cells NC identity, a decrease of the pluripotency gene OCT4 by day 4 (FIGS. 5A-5C) and high expression of the NCC-related genes SOX10 and P75 (FIGS. 5A-5C) (Simões-Costa & Bronner, *Development* 142, 242-257 (2015)) with a peak at day 6 (FIGS. 5A-5C) were shown.

Figure 1C:
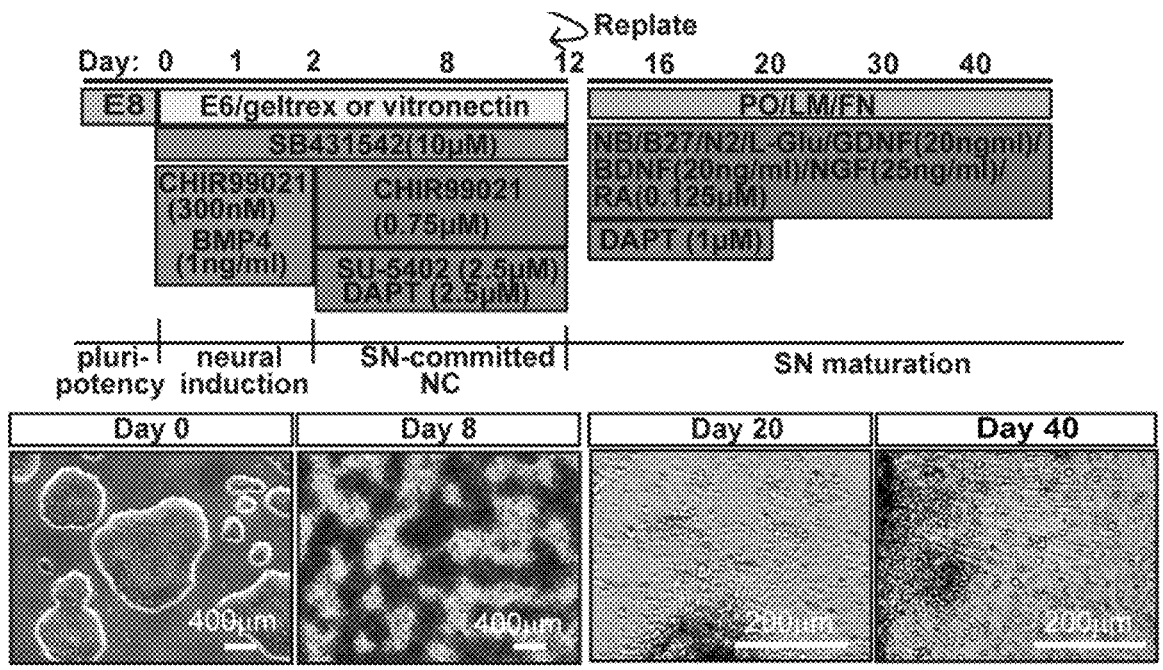
Figure 5D:
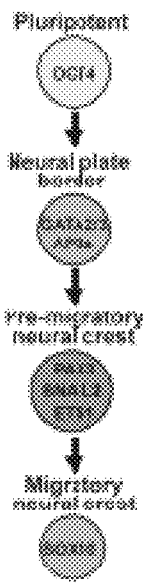

To rapidly generate SNs, FGFR/VEGFR inhibition (SU-5402) and Notch inhibition (DAPT) was used (Chambers, et al., *Nat. Biotechnol.* 30, 715-720 (2012)), to increase SN differentiation efficiency and speed (FIG. 1C). To ensure that the cells still properly passed through the NCC stage (FIG. 5D) it was shown that within the first 4 days OCT4 was extinguished and genes expressed during neural plate border formation (GATA 2/3 and AP2A) (de Crozé, et al., *Proc.*

Figure 1D:
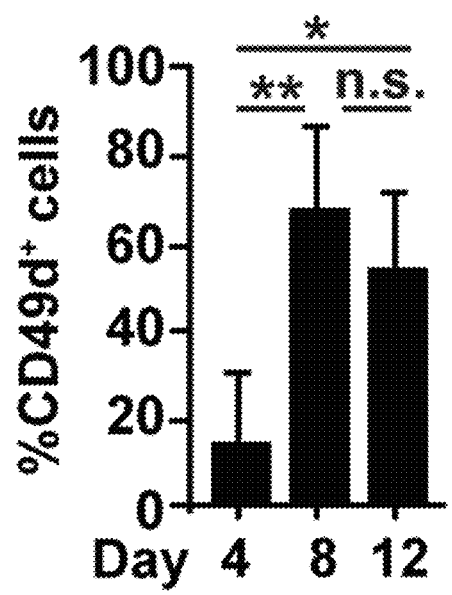
Figure 1E:
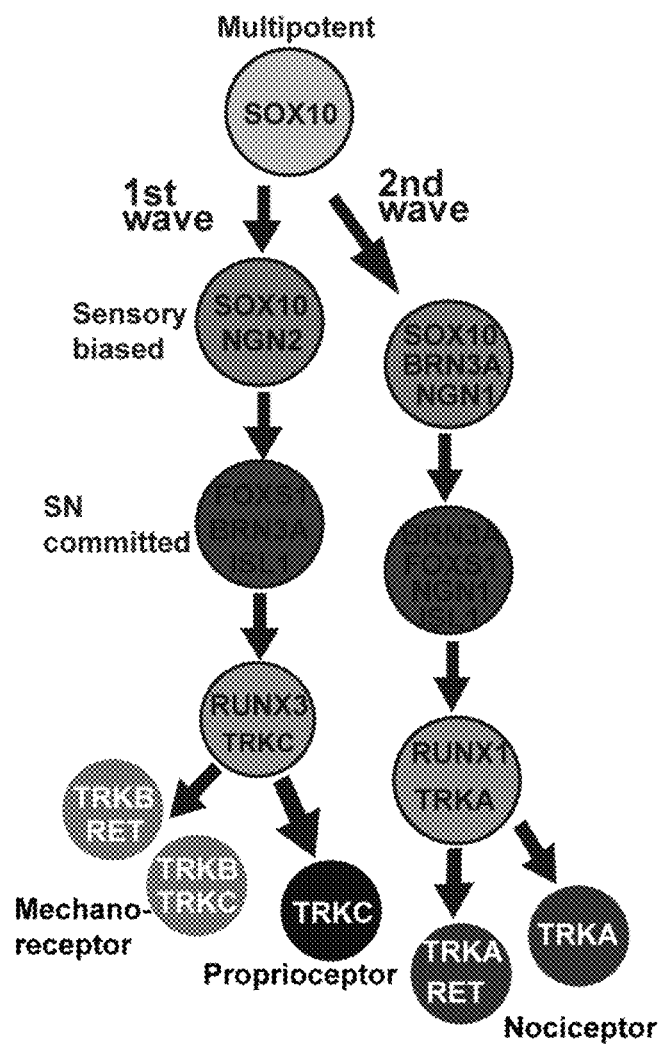
Figure 5E:
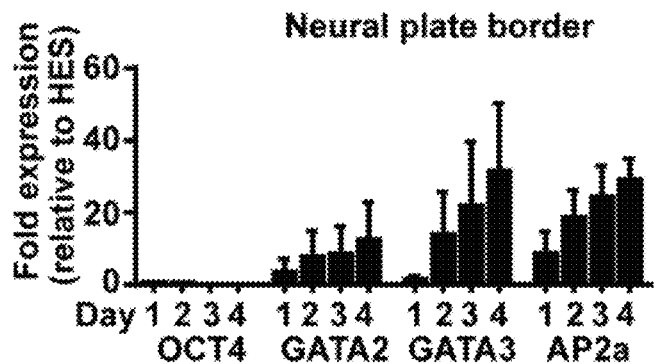
Figure 5F:
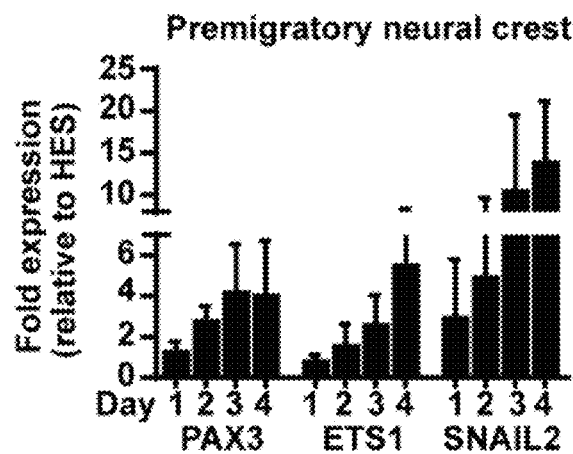
Figure 5G:
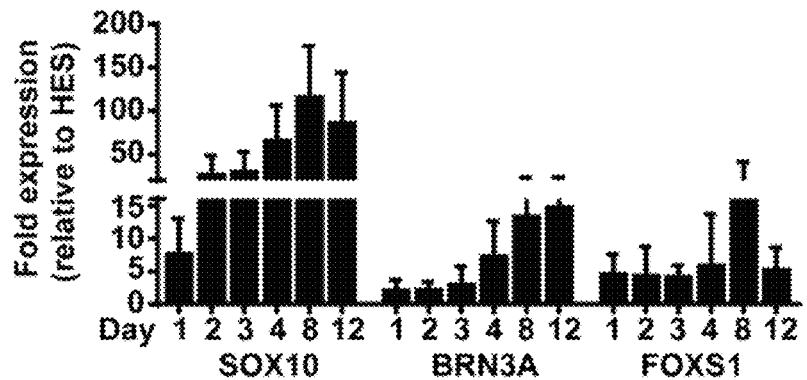
Figure 5H:
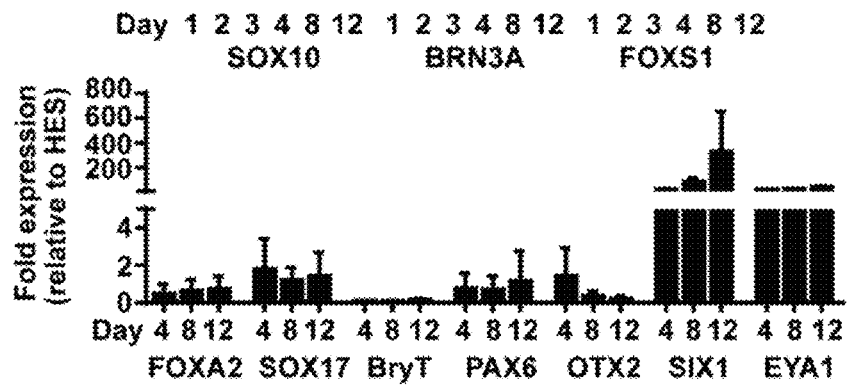

*Natl. Acad. Sci. U.S.A.* 108, 155-160 (2011)) and in specification of premigratory NCCs (PAX3, ETS1 and SNAIL2) (Théveneau, et al., *PLOS ONE* 2, e1142 (2007)) were upregulated (FIGS. 5E and 5F). Expression of CD49D was found in ~70% of cells by day 8 (FIG. 1D). Similar to in vivo studies, expression of AP2A, SOX10, FOXS1 and the SN marker BRN3A (FIGS. 1E and 5G) was found, indicating the presence of SN-committed NCCs. The cultures showed low expression of contaminating endoderm (SOX17/FOXA2), mesoderm (BRYT) and CNS progenitors (PAX6/OTX2, FIG. 5H). However, expression of the placode progenitor SIX1 and EYA1 (Zou, et al., *Development* 131, 5561-5572 (2004)) (FIG. 5H) was seen. Placode and neural crest lineages are intimately associated during development (Lallemend & Ernfors, *Trends Neurosci.* 35, 373-381 (2012)) and placode derivation from hPSCs has some similarities with this protocol (Tchieu, et al., *Cell Stem Cell* 21, 399-410.e7 (2017), Zimmer, et al., *PNAS* 115, E8775-E8782 (2018)).

Figure 5I:
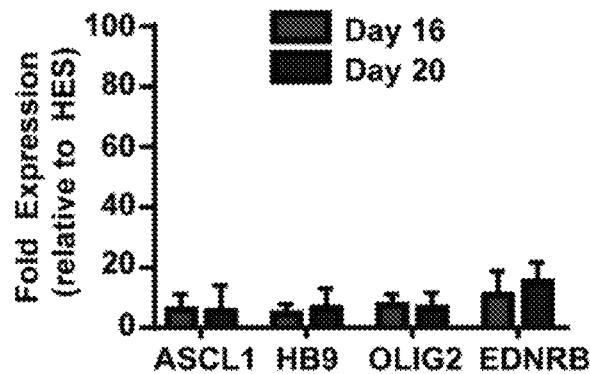
Figure 5J:
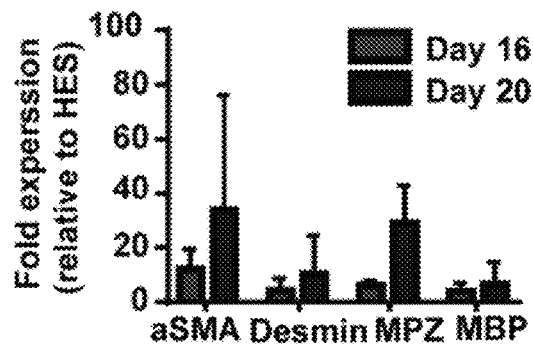

Together, these data support a conclusion that the method induces progression through the proper developmental stages of NCCs, and that FGF and Notch signaling inhibition pushes the differentiation towards a sensory neuron fate. Next, experiments were designed to push the NCCs towards SNs by replating them on day 12 in a combination of SN-favoring growth factors (FIG. 1C) (Chambers, et al., *Nat. Biotechnol.* 30, 715-720 (2012)), with the addition of DAPT (day 12-20), which reduces the number of SOX10+ progenitor cells and enriches the purity of the culture. By day 20, SNs formed defined clusters reminiscent of ganglia and show axonal outgrowth (FIG. 1C, bottom) and 60-70% of all cells expressed the pan-SN marker BRN3A (FIGS. 1F and 1G). Additionally, almost all (~99%) of the TUJ1+ neurons expressed BRN3A, indicating little contamination of other neuronal cell types (FIGS. 1F and 1G). This was confirmed by low expression of markers of autonomic (ASCL1), motor (HB9 and OLIG2), CNS (TBR1) and enteric neurons (EDNRB)(FIG. 5I). However, the remaining 30-40% of the cells in the cultures have a character of myofibroblasts (αSMA, desmin) and Schwann cells (MPZ, MBP) (FIG. 5J), similar to previous reports (Dionisi, et al., *Sci Rep* 10, 1-12 (2020)). PSC differentiations are notoriously variable.

Efforts were made to define the variability in the protocol and found that sequential culture of hESCs resulted in decreased NCC and SN differentiation efficiency over time affecting about one in every five experiments. This limitation could be overcome using the CryoPause method (Wong, et al., *Stem Cell Reports* 9, 355-365 (2017)).

Furthermore, to enhance the ease of working with this protocol, it was shown that the cells can be frozen at the NCC stage (day 12) without compromising further differentiation after thawing. This will allow practitioners to generate large, well characterized batches of cells for their analysis without the compromise of potentially failed experiments.

Figure 1J:
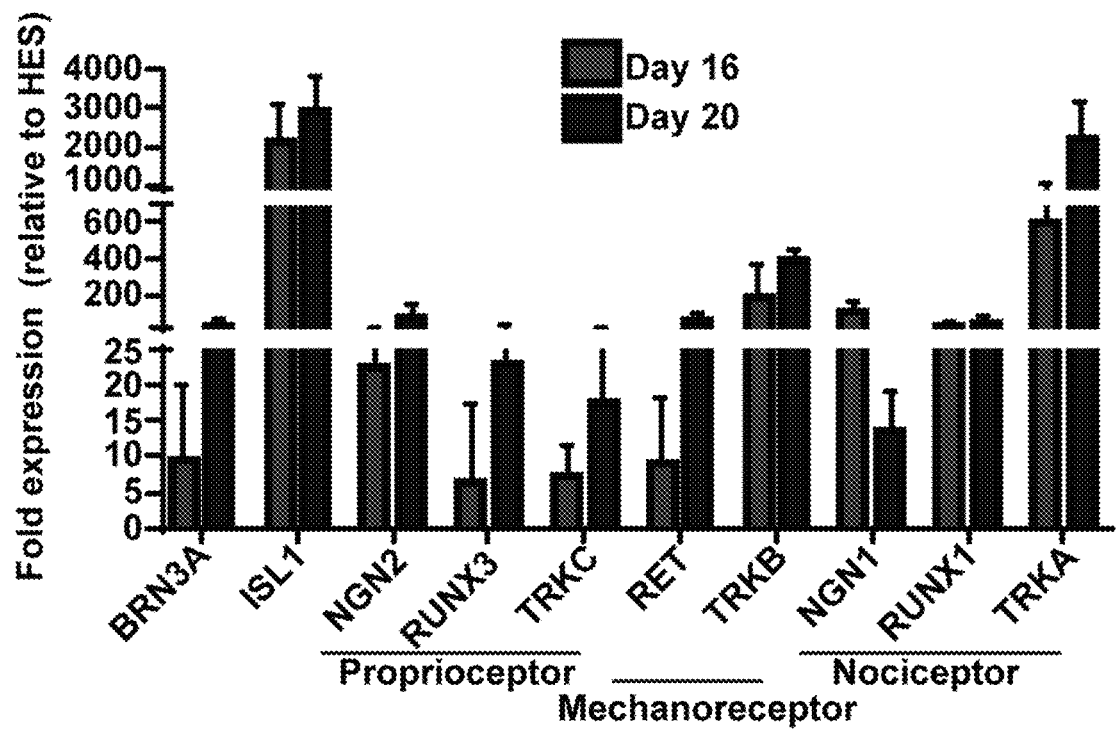

Molecular characterization of the SNs and analysis of the composition of SN subtypes in the cultures revealed robust expression of ISL1, BRN3A, Peripherin (PRPH) and TUJ1, as well as RUNX1+ nociceptor-fated SNs and mechanoreceptor RET+ SNs similar to in vivo studies. FACS analysis and gating on specific cell populations in SSC/FSC according to the expected cell size followed by sorting for their associated TRK receptor was used. For example to detect the portion of nociceptors in the cultures, gating was on the small cell size population (left most gate in FIGS. 1H and 1I) and then selected TRKA+ cells to be ~70% starting at day 20 (~50% of total cells) (FIGS. 1H, 1I, left bars). Accordingly, ~30% of SNs (~34% total cells) were a combination of TRKB+/C+ mechanoreceptors (due to this double staining the numbers add up to more than 100%) and TRKC+ proprioceptors (FIGS. 1H, 1I). This ratio correlates with previous studies that showed the ratio of TRKA+, TRKB+ and TRKC+ neurons in the human DRG is approximately of 2:1:1 (Ernsberger, *Cell Tissue Res* 336, 349-384 (2009)), indicating that cells established in this way resembles the DRG neuronal composition. Finally, RT-qPCR analysis on day 16 and 20 confirmed the presence of each SN subtype (FIG. 1J). In sum, the data shows that the method can be used to generate SNs, which go through the proper developmental stages.

Example 2: Late-Stage Molecular and Functional Characterization of hESC-Derived SNs Materials and Methods
Electrophysiology Experiments were performed using a Maestro Pro (Axion Biosystems) MEA system. CytoView MEA 96 plates containing 8 embedded electrodes/well were coated with PO/LM/FN 448 and seeded with NCCs (day 6 or 12) or SNs (day 30). Repeated recordings were made every 5 days at 37° C. with a sampling frequency of 12.5 kHz for 5 min. Recordings from at least 6 wells were averaged per reading. Bursts were detected using Inter-Spike Interval (ISI). Capsaicin, WIN 55,212 and Pregnenolone were titrated and incubated for 1 min before data acquisition. Hypoosomotic media was obtained by mixing Sensory neuron media with sterile water in a 45:55 ratio, treatment was done for 1 min.
Late Stage Replate On the indicated day, sensory neuron cultures were replated onto plates coated with 15 μg/ml poly-L-ornithine hydrobromide, 2 μg/ml of mouse-laminin-1 and 2 μg/ml human fibronectin. To replate, cells were dissociated with Accutase (Innovative Cell Technologies Inc., 84 #AT-104) for 45 min, washed once with PBS and resuspended in Sensory Neuron Media Cells with a p1000. SNs were then seeded onto the new plates at a density of 250,000 cells/cm2. Cells were fed every 2-3 days through day 20 or every 3-4 days afterwards.
Results Next, the SNs' maturity was functionally characterized and assessed via late stage marker expression and electrophysiology. Beginning on day 20, formation of large clusters with dense, radiating axons were observed. General markers indicating maturation of SNs were present at day 30 (VGLUT1/2/3, FIG. 2A).

Nociceptors expressed SST, PLXNC1 and Substance P (SubP) (FIG. 2A-2D). Expression of the members of the transient receptor (TRP) family TRPV1 and TRPV2 (expressed in medium-to large-diameter nociceptors), the temperature sensitive receptor TRPM8, and the cold-activated receptor TRPA1 (FIG. 2A) were also found. Finally, expression of SCN8A-11A genes (encode Na+ channels Nav1.6-9) and the ATP-activated receptor P2X3 were also investigated.

Similarly, mechanoreceptors expressed the mechanically-activated K+ channels TREK-1 (KCNK2) and TRAAK (KCNK4), the acid-sensing ion channels (ASIC1-3) expressed in the Meissner corpuscles and Merkel cells, NF200 (expressed in myelinated A-βfiber neurons), PIEZO2 (expressed in C-low threshold mechanoreceptors), NECAB2, and FAM19A1 (expressed in low threshold mechanoreceptors).

Proprioceptors expressed SPP1 and Parvalbumin (PVALB). Protein expression of the nociceptor-related marker calcitonin-gene related protein (CGRP) and SubP was confirmed on day 50 by immunofluorescence (FIGS. 2B, 2C, 2D).

Figure 2E:
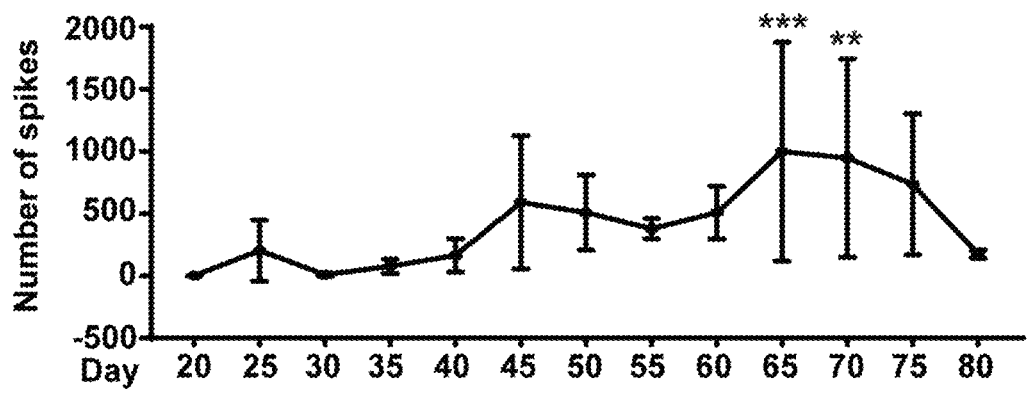
Figure 2F:
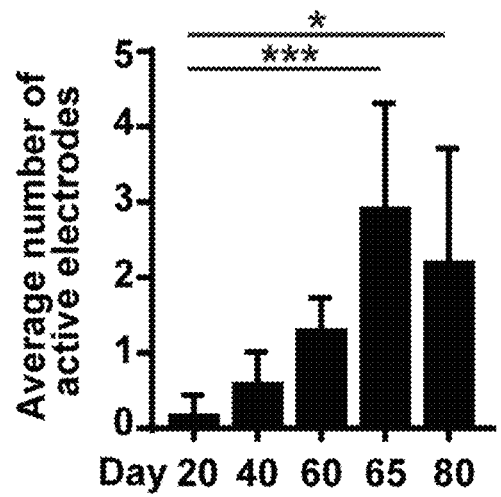
Figure 2G:
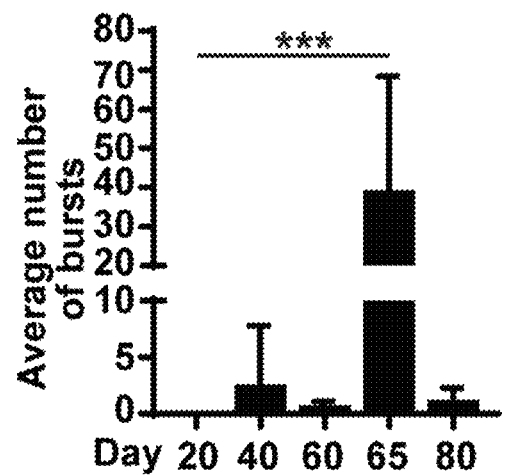
Figure 2H:
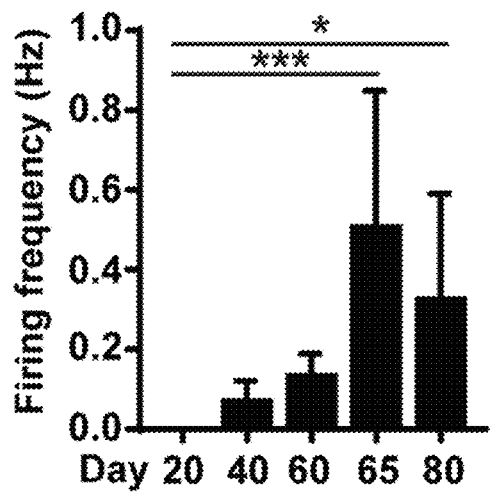
Figure 2I:
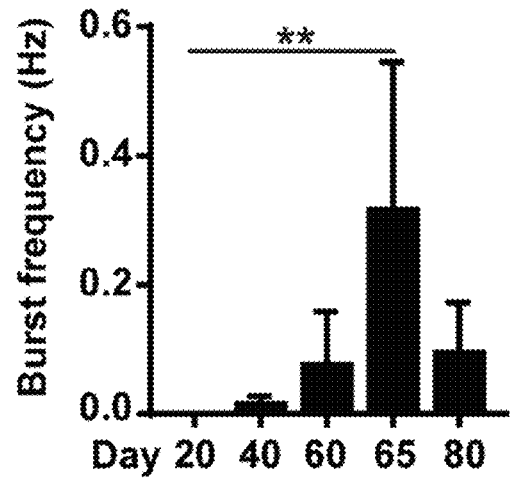
Figure 2J:
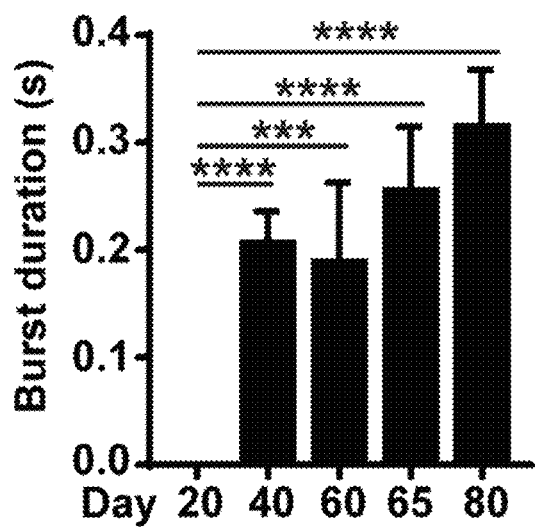

Next, SNs function was investigated. Using multi-electrode array (MEA), spontaneous neural activity was found starting on day 25 and peaking on day 65 (FIG. 2E). By day 65 the number of active electrodes peaked (Nehme, et al., Cell Rep 23, 2509-2523 (2018)), the number of bursts peaked, firing and burst frequency was highest. However, the duration of the bursts increased up to day 80 and correlated with a decrease in burst but not in firing frequency, indicating firing of longer but less frequent bursts. (FIGS. 2F, 2G, 2H, 2I, 2J). Synchronous network activity was not observed. It is unclear whether this is because the SNs are not mature enough or whether PNS neurons do not form networks in vivo and in vitro (Alshawaf, et al., Scientific Reports 8, 603 (2018), Namer, et al., EBioMedicine 39, 401-408 (2019)).

Next specific modulation of the SN subtypes was sought. Nociceptor agonists capsaicin (Caterina, et al., Nature 389, 816-824 (1997)), WIN 55, 212-2 and pregnenolone (Quallo, et al., ELife 6, e26138 (2017)) increased firing rate (FIG. 2K). Additionally, incubation of SNs with hypoosmotic media (mimics pressure) increased the firing rate, indicating that the mechanoreceptors are functional (FIG. 2L).

Long-term culture of SNs (50 days or more) causes neuronal detachment from the wells. Thus, it was investigated whether replating cells a second time would be suitable for long-term cultures. It was found that SNs can be replated anytime between day 16 and day 50 and form a dense network 20 days post-replating.

Figure 6A:
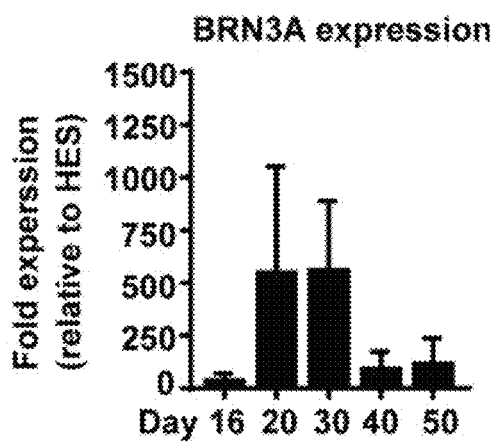
FIGS. 6A-6C illustrate replating of late-stage SNs (related to FIGS. 2A-2L).
Figure 6B:
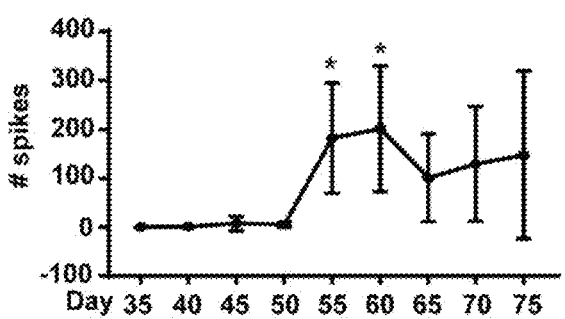
Figure 6C:
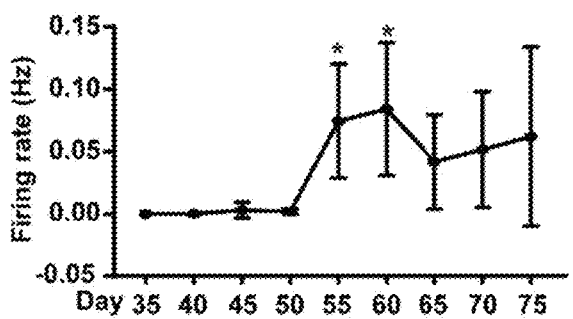

To investigate if this might be used as an axotomy model, two questions were investigated: (i) are the neurons 20 days post-replating truly post-mitotic SNs or were they replenished from SOX10+ progenitor cells left in the cultures and (ii) are the replated neurons electrically active? The cultures have very few SOX10+ cells at day 30, 40, 50. However, it was found that in the normal course of differentiation (when replating at day 12), BRN3A peaks 10-20 days post replating and is downregulated in mature SNs (FIG. 6A). Thus, it was initial thought that if new SNs were being generated from SOX10+ cells at the day 50 replating, then they would show high BRN3A levels 20 days later (day 70). This, however, was not the case. Additionally, SNs replated at day 30 are electrically active 25 days later. In sum, the results show the efficient generation of functional SNs that can be maintained for long-term studies.

Example 3: Strategies for SN Subtype Enrichment

Materials and Methods
Immunopanning

Immunopanning was adapted from (Sloan, et al., Neuron 95, 779-790.e6 (2017)). Three 10 cm petri dishes were coated with 40 µL of anti-mouse IgG or anti-goat IgG in 13 mL of 50 mM Tris-HCl pH 9.5 at 4° C. overnight. The dishes were washed three times with PBS and incubated with 6.6 µg of TRKA, TRKB or TRKC antibody in 5 mL 0.2% BSA+10 µg DNAse in PBS of for at least 2 hours at RT. Day 25 SNs were washed with PBS, incubated with Accutase for 45 min at 37°, collected in PBS and centrifuged at 200 g for 4 min. The pellet was resuspended in Panning buffer (20% BSA, 10 µg DNAse, and 10 µM Y-27632 in PBS using a p1000 micropipette, passed through a 0.22 µm filter and cells were counted. The TRKA panning dish was washed 3 times with PBS. Cells were added and incubated for 15 min at RT and transferred to the next panning dish (TRKB), previously washed 3 times with PBS. This was repeated for the final panning dish. Positive selection plates were carefully washed with PBS six to seven times. Then the dish was incubated with 5 mL of dissociation buffer (1 ml Accutase in 14 mL 1× Earle's balanced salt solution (EBSS) at 37° C. for 5 min. Cells were dislodged with 30% FBS in 50/50 neurobasal medium/DMEM, collected and centrifuged at 200 g for 4 min. The pellet was resuspended in SN differentiation media+10 µM Y-27632 and plated in 96-well plates or concentrated in a 10 µL-drop and plated in well dried 24-well plates coated with PO/LM/FN. The media was replaced the following day.

Results

Figure 7A:
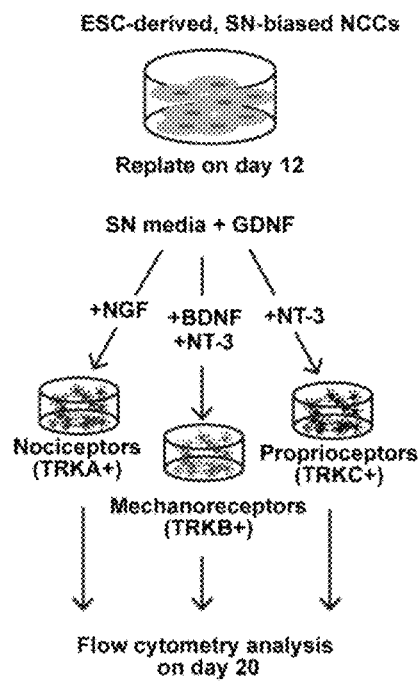
FIGS. 7A-7G illustrates strategies for SN subtype enrichment (related to FIGS. 3A-3F).
Figure 7B:
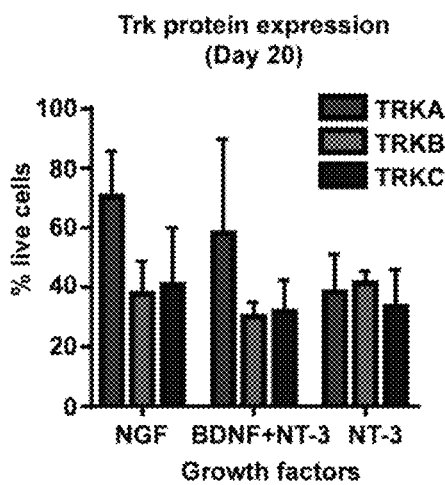
Figure 7C:
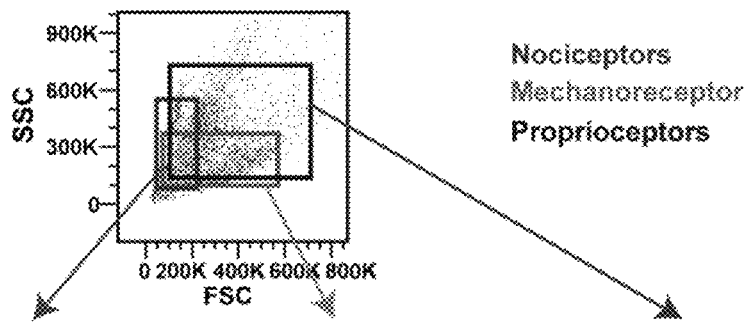
Figures 7D, 7E, 7F:
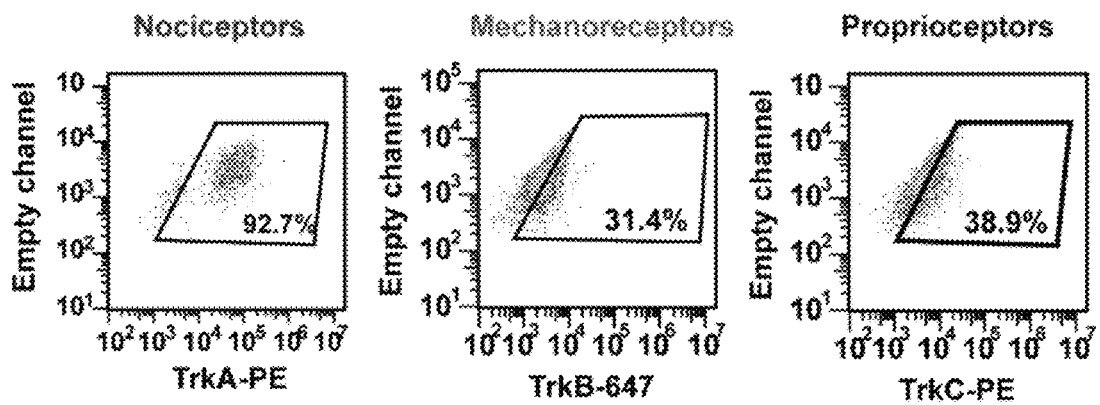

Contrary to previous reports (Alshawaf, et al., Scientific Reports 8, 603 (2018), Chambers, et al., Nat. Biotechnol. 30, 715-720 (2012), Schrenk-Siemens, et al., Nat. Neurosci. 18, 10-550 16 (2015)), the investigated protocol generates all three SN subtypes (FIG. 1H, 1I). Thus, methods to enrich distinct SN subtypes from bulk cultures were investigated. First, NGF, BDNF and NT-3 were used to promote differentiation of nociceptor, mechanoreceptors, and proprioceptors, respectively (Bibel & Barde, Genes Dev. 14, 2919-2937 (2000)) (FIG. 7A). FACS analysis on day 20 however, indicated no subtype enrichment (FIG. 7B). FACS sorting was used to try to isolate/purify SN subtypes (FIGS. 7C, 7D, 7E, 7F). Unfortunately, the sorted cells failed to survive. Finally, immunopanning (Sloan, et al., Neuron 95, 779-790.e6 (2017)), a gentle antibody-based purification technique was investigated to segregate the different SN subtypes (FIG. 3A, left). This method allows the binding of specific cells from a mix to a dish pre-coated with antibodies against cell surface proteins. The cells of interest attach to the antibody and the following wash and dissociation steps are much gentler compared to FACS. It was shown that TRKA+ nociceptors, TRKB+ mechanoreceptors and TRKC+ proprioceptors could be isolated from bulk day 25 SN cultures. Results show that immunopanning allows the isolation/purification of each SN subtype. Isolated TRKB+/TRKC+ SNs were also found.

Figure 3D:
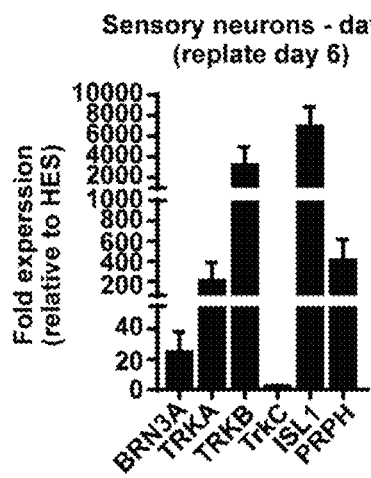
Figure 3E:
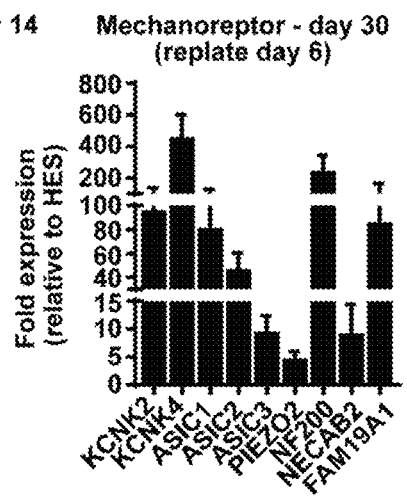
Figure 3F:
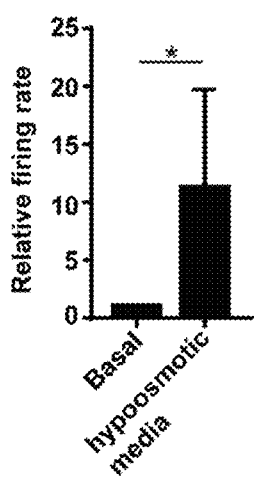

A technically easier approach to enrich for specific SN subtypes by changing the culture conditions in the protocol was also investigated (FIG. 3A, right). SNs develop in vivo in two waves marked by NGN2 followed by NGN1 (Ma, et al., Genes Dev. 13, 1717-1728 (1999)). In the described SN protocol, TUJ1+ neurons were found at day 8, compared to the control NCC protocol. This coincided with NGN2 expression early (day 3) followed by NGN1 expression later (day 8, FIG. 7G), together indicating that both SN development waves occur. Based on these results, whether early replating (which pushes neuron differentiation) would promote NGN2-mediated mechanoreceptor and proprioceptor enrichment (FIGS. 1E and 3B) was tested. The SN-specified NCCs were replated at day 4, 6, 8, 10, 12 and TRK expression was assessed by FACS 8 days later (FIG. 3C). A dramatic enrichment (80%) of TRKB+ mechanoreceptors, when the replate was done at day 6, supporting the belief that this caught the first wave of SN development. However, TRKC+ proprioceptors were not generated at a higher efficiency than in the original bulk protocol (~40%) (FIG. 3C). The mechanoreceptor-enriched cultures expressed pan-SN markers (BRN3A, TUJ1, PRPH, VGLUT3, ISL1 (FIGS. 3D-3F) as well as mechanoreceptor specific markers TRKB, RET, KCKN4, FAM19A1 (FIGS. 3D and 3E) and specifically responded to hypoosmotic pressure (FIG. 3F) at a higher level compared to bulk cultures (FIGS. 2K, 2L). In sum, results show two methods (immunopanning and catching the first SN development wave) to enrich for specific SN subtypes from the cultures.

Figure 4A:
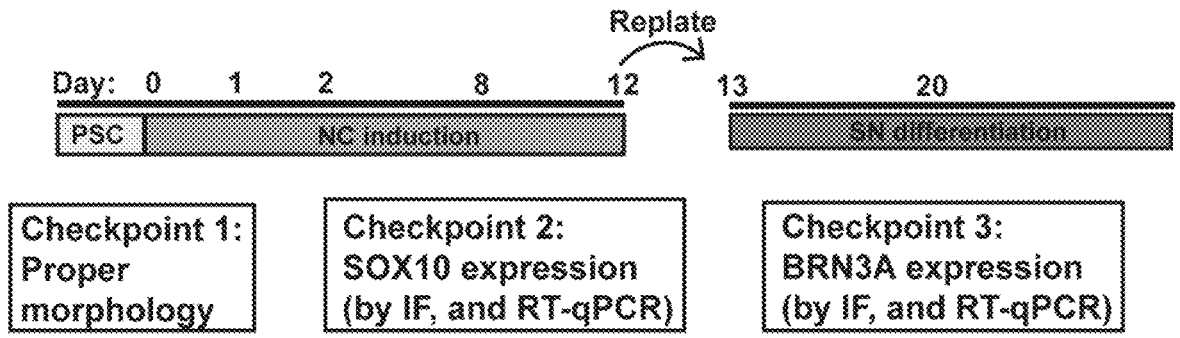
FIGS. 4A-4D illustrate differentiation of SNs from iPSCs.
Figure 4B:
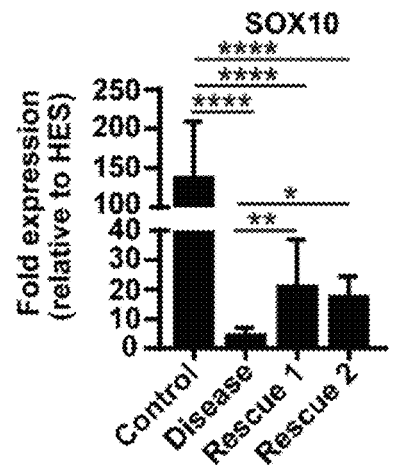
Figure 4C:
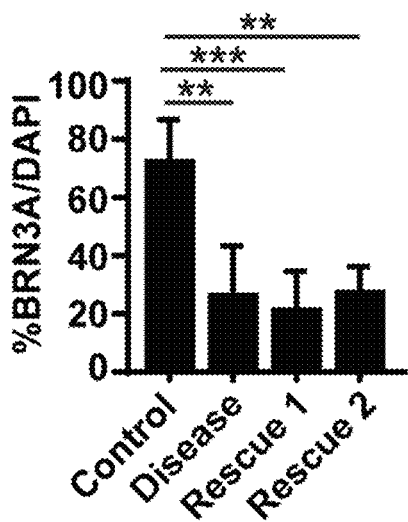
Figure 4D:
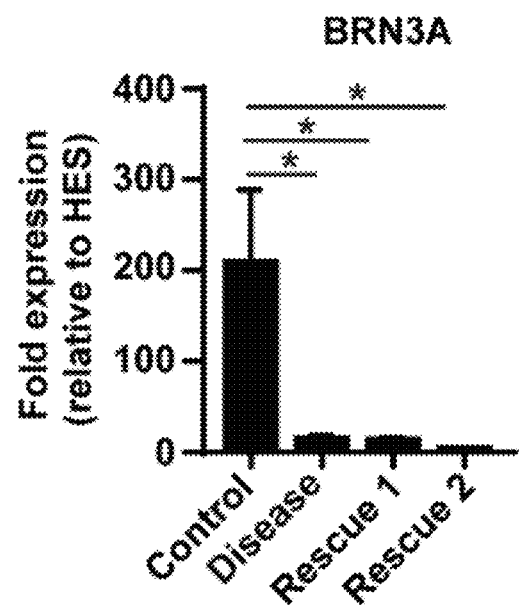

Example 4: Efficient SN Differentiation of Patient-Derived Induced Pluripotent Stem Cells For successful disease modeling, drug screening and future cell replacement approaches it is important that differentiation protocols work appropriately with iPSCs. Thus, here Familial Dysautonomia (FD), a devastating disorder caused by a mutation in the ELP1 gene that decreases the numbers of SNs (Norcliffe-Kaufmann, et al., *Prog. Neurobiol.* 152, 131-148 (2017)), was investigated as model disease. Differentiations included previously characterized (Zeltner, et al., *Nat. Med.* 22, 1421-1427 (2016)) healthy control iPSCs (Control), FD patient-derived iPSCs (Disease), and FD iPSCs where the ELP1 mutation was rescued using CRISPR-Cas9 (Rescue 1 and Rescue 2, i.e. two clones) into SNs. To confirm that the differentiation is properly occurring, a series of quality control checkpoints were tested (FIG. 4A). Checkpoint 1: Proper NCC generation is indicated by dense ridges (arrow) in Control and Rescue 1/2, but are diminished in Disease. Checkpoint 2: These NCCs express high levels of SOX10 in Control, somewhat diminished in Rescue 1/2 and drastically reduced in Disease. Checkpoint 3: Control iPSCs generated SNs properly (~75% BRN3A+ 227 SNs), while Disease, Rescue 1 and 2 were deficient (~25%, FIGS. 4C, 4D). Overall, rescuing ELP1 increased the number of NCCs, but did not rescue the SN phenotype, indicating that ELP1 is important for NCC development, but another mechanism is responsible for the SN defect in FD, agreeing with previous results (Zeltner, et al., *Nat. Med.* 22, 1421-1427 (2016)). Together, these results show that the provided protocol 1) can be utilized for both hESCs and iPSCs and 2) is capable of recapitulating disease phenotypes observed in FD.

Collectively, the foregoing experiments exemplify an efficient and versatile method to derive SNs from hPSCs. Differentiation is a chemically defined monolayer culture, which bypasses the need to generate neurospheres (Alshawaf, et al., *Scientific Reports* 8, 603 (2018), Boisvert, et al., *Sci Rep* 5, 16821 (2015), Schrenk-Siemens, et al., *Nat. Neurosci.* 18, 10-550 16 (2015), Young, et al., *Mol Ther* 22, 1530-1543 (2014)) with only one replating step (day 12) (Alshawaf, et al., *Scientific Reports* 8, 603 (2018), Boisvert, et al., *Sci Rep* 5, 16821 (2015), Young, et al., *Mol Ther* 22, 1530-1543 (2014)). Culturing aids to reduce variability were included by using the CryoPause method (Wong, et al., *Stem Cell Reports* 9, 355-365 (2017)) as well as a mid-differentiation freezing option. By day 20, an efficiency of 60-70% of all cells being BRN3A+ and almost all of those (99%) being TUJ1+ SNs (FIG. 1F, 1G) was reached.

It has been shown that H9 cells are prone to differentiate into SNs. Interestingly, SN differentiation from control iPSC was more efficient (~70%) compared to H9 cells, indicating that the efficiency observed is due to the protocol and not any intrinsic mechanism in H9 cells. By day 20, the SN cultures are composed of all three SN subtypes: nociceptors, mechanoreceptors and proprioceptors (FIGS. 1H, 1I) at a ratio of approximately 2:1:1, which correlates with the relative SN distribution in the human DRG in vivo (Ernsberger, *Cell Tissue Res* 336, 349-384 (2009)). Accordingly, between day 30 and 50, the expression levels of TRKA declines, which mimics what happens in vivo, as a subset of nociceptors downregulate the expression of TRKA after birth (FIG. 1H, 1I) (Ernsberger, *Cell Tissue Res* 336, 349-384 (2009)). Thus provided is an in vitro model that can be used to study the neuronal interactions within ganglia. Expression of SN progenitor (FIG. 1J) and mature markers (FIG. 2A-2D) of each subtype are reported. For example, high expression of RET (co-expressed in 50% of TRKA+ human SNs)(FIG. 1J), TRPA1 (expressed in almost all TRPV1+ TRKA+ human SNs)(FIG. 2A), as well as the Na channels SCN8A-11A, were found in agreement with a previous report in human DRG (Rostock et al., *Neuroscience,* 387, pp. 13-27 (2018)). Lastly, the SNs are functionally active and respond to specific stimuli, including nociceptive agonists or hypoosmotic pressure (FIGS. 2E-2L).

Previous reports have shown generation of nociceptors, mechanoreceptors and proprioceptors (Alshawaf, et al., *Scientific Reports* 8, 603 (2018)), albeit at a lower efficiency (up to 11% of BRN3A+/ISL1+ cells) and the percentage of TRKA+, TRKB+ and TRKC+ SNs range from 17% to 25%. Another report (Schrenk-Siemens, et al., *Nat. Neurosci.* 18, 10-550 16 (2015)) showed directed differentiation of hPSC to mechanoreceptors reaching up to ~28% when combined with mitotic blockers and ~18% upon lentivirus-mediated overexpression of NGN2, which may blur results if used for modeling SN disorders. The provided bulk SN protocol reaches better efficiencies. Additionally, the efforts to develop methods for the enrichment of each SN subtype provides the possibility to generate nociceptors at ~90%, proprioceptors at ~38% (by FACS/Immunopanning, FIGS. 7C-7F) and mechanoreceptors at ~75% (by day 6 replating). In the molecular characterization of these mechanoreceptors, expression of NECAB2, FAM19A1, KCNK2, KCNK4 and PIEZO2 (FIGS. 3D and 3E) was found, similar to previous reports of hPSC-derived SNs (Alshawaf, et al., *Scientific Reports* 8, 603 (2018), Nickolls, et al., *Cell Rep* 30, 932-946.e7 (2020)). Also found was the ASIC family of genes which have a modulatory role in mechanotransduction (Delmas & Rodat-Despoix, *Nature Reviews Neuroscience* 12, 139-153 (2011)) as well as NF200 expression. These genes were found to be expressed in mouse DRG, but human DRG gene expression might be different. For example, recent evidence from human DRG shows that NF200 is expressed in nearly all SNs (Rostock, et al., *Neuroscience,* 387, pp. 13-27 (2018)). Future transcriptomics analysis of the hPSC-derived DRG-like culture might provide more clarity into these species' differences.

Lastly, a recent study showed a method to generate proprioceptors (70% of SNs) from SOX10+ NCCs using high concentrations of NT-3 and low concentrations of NGF, GDNF, and BDNF (Dionisi, et al., *Sci Rep* 10, 1-12 (2020)). The authors also see increases of NGN1 and NGN2 expression. Thus, it is possible that modifying the growth factor concentrations in the provided system could enrich the culture with TRKC+ proprioceptors.

Figure 7G:
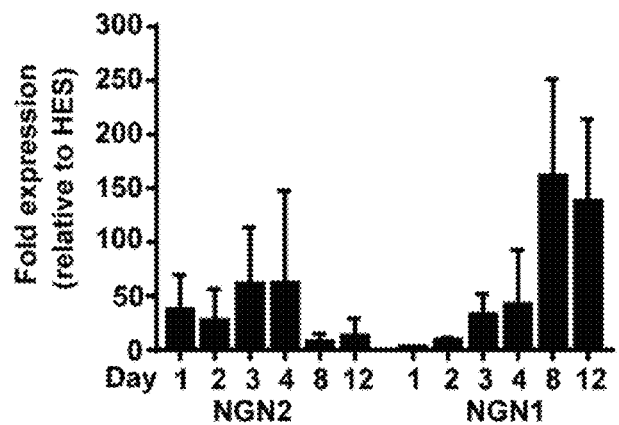

Results show that the SNs generated by this protocol can be replated in late stages of differentiation and still be viable and functional (FIGS. 7A-7G). It was initially believed that these SNs were differentiated from SOX10+ progenitor cells. In this scenario, BRN3A expression would be seen within 30 days of replating based on the RT-qPCR analysis (FIG. 7G). However, because BRN3A expression 20 day post-replate was not seen, it is believed that fully differentiated SNs are being replated, which are also functional by electrophysiology analysis. This indicates that the proposed protocol could be used as a model to study peripheral axotomy in vitro. In conclusion, a versatile protocol for the generation of functional SNs that mimic the proportions of subtypes in the DRG has been developed. Several methods can be employed to isolate each of the specific SN subtypes, nociceptors, mechanoreceptors and proprioceptors from these cultures. This protocol can be adapted for a myriad of research interests ranging from studying the human DRG to investigating PNS diseases such as FD using patient-derived iPSCs that affect either all SN subtypes or each of the individual subtypes, and the work can be used to further advance numerous fields interested in studying the functions of, and diseases associated with, human SNs.

Additional Materials

TABLE 1

| Reagents | | |
|---|---|---|
| Reagent | Company | Catalog number |
| Human embryonic stem cells | WiCell | #WA-09 |
| Essential 8 Medium | Gibco | #A1517001 |
| Essential 8 Medium supplement | Gibco | #A1517101 |
| vitronectin | Gibco | #A27940 |
| PBS | Corning | #21-031-CM |
| EDTA | ThermoFisher | #AM9262 |
| NaCl | Sigma | #S7653 |
| Geltrex | Invitrogen | #A1413202 |
| Essential 6 Medium | Gibco | #A1516401 |
| SB431542 | R&D | #1614 |
| BMP4 | R&D | #314-BP |
| CHIR99021 | R&D | #4423 |
| Y-27632 | Peprotech | #1293823 |
| SU5402 | Biovision | #1645-1 |
| DAPT | R&D | #2634 |
| poly-L-ornithine hydrobromide | Sigma | #P3655 |
| mouse-laminin-1 | Cultrex | #3400-010-02 |
| human fibronectin | Corning | #356008 |
| Accutase | Innovative Cell Technologies Inc. | #AT-104 |
| Neurobasal media | Gibco | #21103-049 |
| N2 supplement | Gibco | #17502-048 |
| B-27 supplement | Gibco | #12587-010 |
| L-glutamine | Life Technologies | #25030-081 |
| GDNF | Peprotech | #450-10 |
| BDNF | R&D | #248-BD |
| NGF | Peprotech | #450-01 |
| retinoic acid | Sigma | #R2625 |
| NT-3 | Peprotech | #450-03 |
| 4% paraformaldehyde | FisherScientific | #AAJ19943K2 |
| BSA | Sigma | #A4503 |
| Triton-X | Sigma | #X100 |
| Goat serum | Sigma | #S26 |
| Donkey serum | Sigma | #S30 |
| DAPI | Sigma | #D9542 |
| Trizol reagent | LifeTechnologies | #15596018 |
| iScript cDNA Synthesis kit | BioRad | #1708891 |
| SYBR Green Supermix | BioRad | #1725270 |
| DMEM | Life Technologies | #11965-092 |
| FBS | Atlanta Biologicals | #S11150 |
| DNAse | ROCHE | # 10104159001 |
| Y-27632 | Peprotech | #1293823-10MG |
| Earle's balanced salt solution | Sigma | #E7510 |
| CytoView MEA 96 plate | Axion Biosystems | #M768-tMEA-96 |
| Capsaicin | Sigma | # M2028 |
| WIN 55,212 | R&D Bio-Techne | #1038 |
| Pregnenolone | Sigma | #P162 |

TABLE 2

| Cell Lines | | | | | | |
|---|---|---|---|---|---|---|
| Cell line | Type | Alternative name | ELP1 expression | Described in | Fibroblast source | FIG. |
| H9 | ESC | WA09 | WT | | WiCell | 1, 2, 3, 5, 6, 7, 8 |
| Control | iPSC | C1 | WT | Zeltner et al., 2016 | Coriell (GM00316) | 1H, 4 |
| Disease | iPSC | S2 | Downregulated | Zeltner et al., 2016 | Coriell (GM04899) | 4 |
| Rescue 1 | iPSC | S2-rescue 1 | WT | Zeltner et al., 2016 | Coriell (GM04899) | 4 |
| Rescue 2 | iPSC | S2-rescue 5 | WT | Zeltner et al., 2016 | Coriell (GM04899) | 4 |

TABLE 3

Antibodies

| Antibodies | Company | Catalog number | Dilution |
|---|---|---|---|
| AP2a | Abcam | #ab108311 | 1:500 |
| ASCL1/MASH1 | Bd Pharmingen | #556604 | 1:100 |
| αSMA | Sigma | #A5528 | 1:1000 |
| Brn3a | Chemicon | #MAB1585 | 1:100 |
| CGRP | Neuromics | #RA242112 | 1:100 |
| Isl1 | DSHB | #39.4D5-c | 1:200 |
| Peripherin | Santa Cruz | #SC-377093/H0112 | 1:200 |
| Ret1 | Sigma | #SAB1409600 | 1:100 |
| Runx1 | Sigma | #HPA004176 | 1:75 |
| Sox10 | Santa Cruz | #sc-365692 and #sc-17342 | 1:100 |
| Substance P | Neuromics | #GP14103 | 1:100 |
| TBR1 | Millipore | #AB10554 | 1:1000 |
| TUJ1 | Biolegend | #802001 and #801201 | 1:1500 |
| Alexa Fluor 488 donkey α mouse | invitrogen | #A21202 | 1:400 |
| Alexa Fluor 488 donkey α goat | invitrogen | #A11055 | 1:400 |
| Alexa Fluor 647 donkey α rabbit | invitrogen | #A31573 | 1:400 |
| Alexa Fluor 647 donkey α mouse | invitrogen | #A31571 | 1:400 |
| Alexa Fluor 488 donkey α rabbit | invitrogen | #A21206 | 1:400 |
| Alex Fluor 488 goat α mouse IgG1 | invitrogen | #A21121 | 1:400 |
| Alexa Fluor 647 goat α mouse IgG2 | invitrogen | #A21241 | 1:400 |
| CD49d-PE/Cy7 | Biolegend | #304314 | 1:20 |
| TRKA-PE | R&D | #FAB1751P | 1:20 |
| TRKB-AF647 | R&D | #FAB3971R | 1:20 |
| TRKC-PE | R&D | #FAB373P | 1:20 |
| anti-mouse IgG | Jackson ImmunoResearch | #115-005-003 | 1:325 |
| anti-goat IgG | Jackson ImmunoResearch | #705-005-003 | 1:325 |
| TRKA | R&D | MAB1751R | 1:100 |
| TRKB | R&D | MAB3971 | 1:100 |
| TRKC | R&D | AF373 | 1:100 |

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

We claim:

1. A method of making sensory neurons comprising culturing of stem cells in monolayer in chemically-defined differentiation media for sufficient duration for the cells to differentiate into sensory neurons comprising nociceptors, mechanoreceptors, and proprioceptors in a ratio similar to those found in dorsal root ganglia,
  wherein, beginning on day zero or day one after plating, the stems cells are cultured in a first differentiation media comprising 5 μM to 10 μM inclusive of a TGFβ/Activin-Nodal signaling inhibitor, 0 ng/ml to 5 ng/ml of a bone morphogenic protein (BMP), and 100 nM to 500 nM inclusive of a Wnt signaling activator.

2. The method of claim 1, wherein the cells are cultured on a vitronectin substrate.

3. The method of claim 1, wherein differentiation is initiated the same day as seeding the stem cells.

4. The method of claim 1, wherein the differentiation media comprises a Wnt signaling activator, a FGFR/VEGFR inhibitor, and a Notch inhibitor.

5. The method of claim 4, wherein Wnt signaling activator is CHIR99021 optionally in a concentration of about 300 nM.

6. The method of claim 1, wherein the method induces differentiation of about 60-70% of the cells into sensory neurons.

7. The method of claim 1 comprising one or more replatings.

8. The method of claim 1 further comprising enriching for mechanoreceptors, nociceptors, and/or proprioceptors.

9. The method of claim 8 further comprising FACS and/or immunopanning to enrich one or more of nociceptors, mechanoreceptors, and/or proprioceptors.

10. The method of claim 1 further comprising isolating sensory neurons, nociceptors, mechanoreceptors, proprioceptors, or a combination thereof from other cells in the culture.

11. The method of claim 1 further comprising making one or more genetic modifications to the genome of the sensory neurons and/or introducing into the sensory neurons one or more nucleic acid expression constructs.

12. A population of cells formed according to the method of claim 1.

13. A composition comprising a population of cells formed according to the method of claim 1.

14. The composition of claim 13 comprising a matrix or substrate for the cells.

15. The composition of claim 13 comprising a pharmaceutically acceptable carrier.

16. A method of treating a subject in need thereof, optionally wherein the subject has a peripheral neuron disorder or a neurodegenerative disease comprising administering the subject an effective amount of the cells formed according to the method of claim 1.

17. The method of claim 1, wherein the BMP is BMP.

18. The method of claim 1, comprising, beginning on day two or three after plating, culturing the cells in a second differentiation media comprising 5 μM to 10 μM inclusive of the TGFβ/Activin-Nodal signaling inhibitor, 0.25 μM to 1.5 μM inclusive of the Wnt signaling activator, 1 μM to 5 μM inclusive of an FGFR inhibitor, and 1 μM to 5 μM inclusive of a Notch inhibitor.

19. The method of claim 18, wherein the TGFβ/Activin-Nodal signaling inhibitor is SB431542, the Wnt signaling activator is CHIR99021, the FGFR inhibitor is SU5402, and the Notch inhibitor is DAPT.

20. A method of making sensory neurons comprising culturing of stem cells for five days in monolayer in chemically-defined differentiation media to induce differentiation of the stems cells into sensory neurons, and replating the cells on day six to increase generation of mechanoreceptors relative to nociceptors and proprioceptors.

* * * * *